United States Patent [19]

Lepper, Jr. et al.

[11] Patent Number: 5,743,262
[45] Date of Patent: Apr. 28, 1998

[54] BLOOD GLUCOSE MONITORING SYSTEM

[75] Inventors: James M. Lepper, Jr., Trabuco Canyon; Mohamed Kheir Diab, Mission Viejo, both of Calif.

[73] Assignee: Masimo Corporation, Irvine, Calif.

[21] Appl. No.: 479,164

[22] Filed: Jun. 7, 1995

[51] Int. Cl.$^6$ ........................................ A61B 5/000
[52] U.S. Cl. ........................................ 128/633
[58] Field of Search ........................ 128/633, 664–7; 356/39–41

[56] References Cited

U.S. PATENT DOCUMENTS

| | | |
|---|---|---|
| 3,740,144 | 6/1973 | Walker . |
| 4,621,643 | 11/1986 | New, Jr. et al. ............... 128/633 |
| 4,927,264 | 5/1990 | Shiga et al. . |
| 4,975,581 | 12/1990 | Robinson et al. ............. 128/633 |
| 5,111,817 | 5/1992 | Clark et al. . |
| 5,127,406 | 7/1992 | Yamaguchi ................... 128/633 |
| 5,313,941 | 5/1994 | Braig et al. ................... 128/633 |
| 5,337,745 | 8/1994 | Benaron ......................... 128/633 |
| 5,355,880 | 10/1994 | Thomas et al. ............... 128/633 |
| 5,372,136 | 12/1994 | Steuer et al. . |
| 5,435,309 | 7/1995 | Thomas et al. ............... 128/633 |
| 5,529,755 | 6/1996 | Higashio et al. ............. 128/633 |

FOREIGN PATENT DOCUMENTS

| | | |
|---|---|---|
| 444934 | 9/1991 | European Pat. Off. . |
| 631137 | 12/1994 | European Pat. Off. . |
| 90/07905 | 7/1990 | WIPO . |
| 93/20745 | 10/1993 | WIPO . |

*Primary Examiner*—Jennifer Bahr
*Assistant Examiner*—Bryan K. Yarnell
*Attorney, Agent, or Firm*—Knobbe, Martens, Olson & Bear

[57] ABSTRACT

A blood glucose monitoring system includes a broadband light source and a specially fabricated optical filter for modulating optical radiation to be transmitted through a fleshy medium. Optical radiation which passes through the fleshy medium is detected by an optical detector which generates an electrical signal indicative of the intensity of the detected light. Digital signal processing is performed on the electrical signal to extract those optical characteristics of the electrical signal due to the optical characteristics of the filter and constituents of the fleshy May 1, 1995 medium other than blood glucose concentration. The monitoring system employs a unique "double-log" transformation to minimize errors due to indeterminate path length variations of the optical radiation through the fleshy medium. The monitoring system further employs specialized signal processing to avoid inaccuracies due to the previously unidentified solvent effect which arises when glucose is dissolved into water.

22 Claims, 14 Drawing Sheets

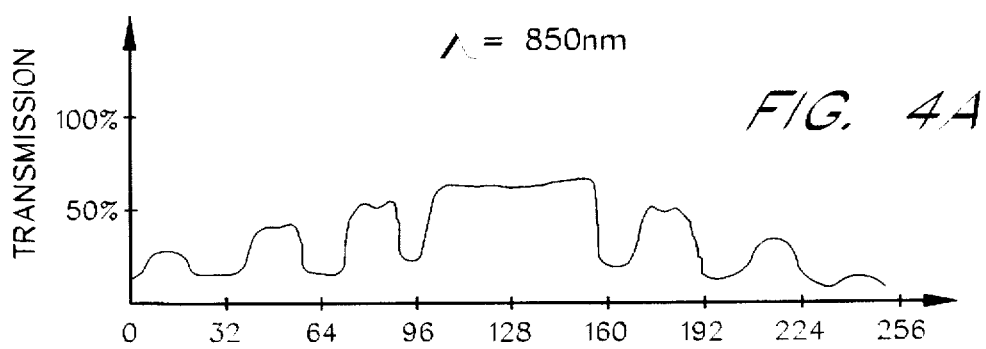
FIG. 4A
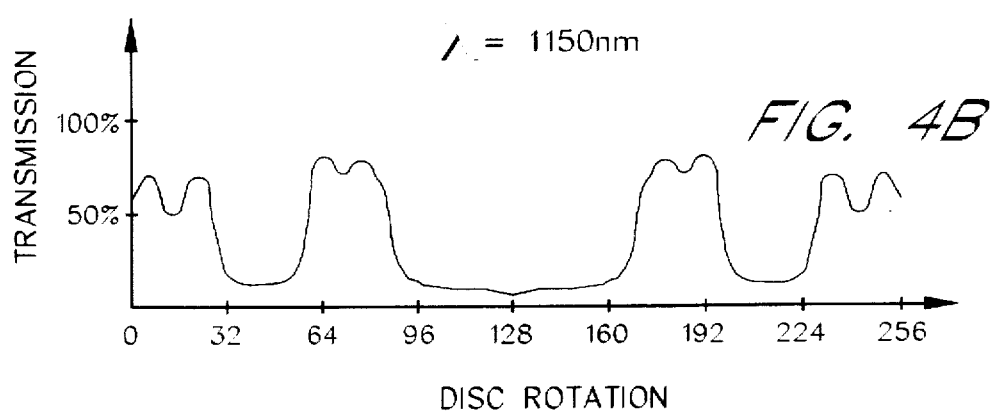
FIG. 4B
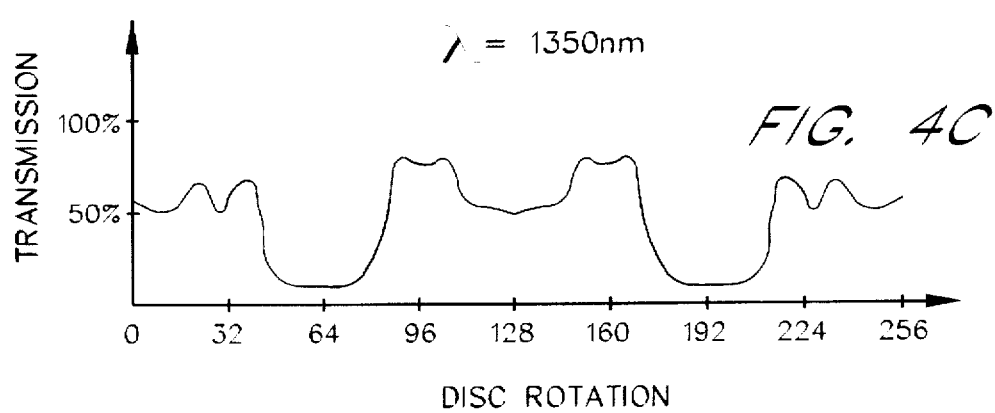
FIG. 4C
$$\begin{bmatrix} f_{\varphi_1',1} & f_{\varphi_1',2} & \cdots & f_{\varphi_1',n} \\ f_{\varphi_2',1} & f_{\varphi_2',2} & & \cdot \\ \vdots & & \cdot & \cdot \\ f_{\varphi_m',1} & \cdots & & f_{\varphi_m',n} \end{bmatrix}$$
FIG. 4D

BLOOD GLUCOSE MONITORING SYSTEM

BACKGROUND OF THE INVENTION

1. Field of the Invention

The present invention relates to noninvasive systems for monitoring blood glucose and other blood constituent concentrations.

2. Description of the Related Art

In the past, many systems have been developed for monitoring blood characteristics. For example, devices have been developed which are capable of determining such blood characteristics as blood oxygenation, glucose concentration, and other blood characteristics. However, significant difficulties have been encountered when attempting to determine blood glucose concentration accurately using noninvasive blood monitoring systems.

The difficulty in determining blood glucose concentration accurately may be attributed to several causes. First, blood glucose is typically found in very low concentrations within the bloodstream (e.g., on the order of 100 to 1,000 times lower than hemoglobin) so that such low concentrations are difficult to detect noninvasively, and require a very high signal-to-noise ratio. Second, there has been a lack of recognition of the kinds of noise and the proper method to use when removing this noise. For example, noise can be classified as deterministic (definable) or stochastic (random) where either of these kinds of noise could be linear (added) or modulated (multiplied). Knowledge of the distinction between the various kinds of noise is essential for purposes of using the proper method of removing noise. Additionally, the optical characteristics of glucose are very similar to those of water which is found in a very high concentration within the blood. Thus, where optical monitoring systems are used, the optical characteristics of water tend to obscure the characteristics of optical signals due to low glucose concentration within the bloodstream. Furthermore, since each individual has unique blood properties, each measurement typically requires calibration for the particular individual.

In an attempt to accurately measure blood glucose levels within the bloodstream, several methods have been used. For example, one method involves drawing blood from the patient and separating the glucose from the other constituents within the blood. Although highly accurate, this method requires drawing the patient's blood, which is less desirable than noninvasive techniques, especially for patients such as small children or anemic patients. Furthermore, when blood glucose monitoring is used to control the blood glucose level, blood must be drawn three to six times per day, which may be both physically and psychologically traumatic for a patient. Other methods contemplate determining blood glucose concentration by means of urinalysis or some other method which involves pumping or diffusing blood fluid from the body through vessel walls. However, such an analysis tends to be less accurate than a direct measurement of glucose within the blood, since the urine, or other blood fluid, has passed through the kidneys. This problem is especially pronounced in diabenics. Furthermore, acquiring urine samples is often inconvenient.

Another proposed method of measuring blood glucose concentration is by means of optical spectroscopic measurement. In such devices, light of multiple wavelengths may be used to illuminate a relatively thin portion of tissue, such as a fingertip or an earlobe, so that a spectrum analysis can be performed to determine the properties of the blood flowing within the illuminated tissue. Although such a method is highly desirable due to its noninvasive character and its convenience to the patient, problems are associated with such methods due to the difficulty in isolating each of the elements within the tissue by means of spectroscopic analysis. The difficulty in determining blood glucose concentration is further exacerbated due to the low concentration of glucose within blood, and the fact that glucose in blood has very similar optical characteristics to water. Thus, it is very difficult to distinguish the spectral characteristics of glucose where a high amount of water is also found, such as in human blood.

As is well known in the art, different molecules, typically referred to as constituents, contained within the medium have different optical characteristics so that they are more or less absorbent at different wavelengths of light. Thus, by analyzing the characteristics of the fleshy medium at different wavelengths, an indication of the composition of the fleshy medium may be determined.

Spectroscopic analysis is based in part upon the Beer-Lambert law of optical characteristics for different elements. Briefly, Beer-Lambert's law states that the optical intensity of light through any medium comprising a single substance is proportional to the exponent of the path lengths through the medium times the concentration of the substance within the medium. That is, $$I = I_o e^{-(pl \cdot c)} \quad (1)$$

where pl represents the path length through the medium and c represents the concentration of the substance within the medium. For optical media which have several constituent substances, the optical intensity of the light received from the illuminated medium will be proportional to the exponent of the path length through the medium times the concentration of the first substance times an optical absorption coefficient associated with the first substance, plus the path length times the concentration of the second substance times the optical absorption coefficient associated with the second substance, etc. That is, $$I = I_o e^{-(pl \cdot c1 \cdot \epsilon 1 + pl \cdot c2 \cdot \epsilon 2 + etc.)} \quad (2)$$

where $\Sigma$ represents the optical absorption coefficient.

SUMMARY OF THE INVENTION

Due to the parameters required by the Beer-Lambert law, the difficulties in detecting glucose concentration arise from the difficulty in determining the exact path length through a medium (resulting from transforming the multi-path signal to an equivalent single-path signal), as well as difficulties encountered due to low signal strength resultant from a low concentration of blood glucose. Path length through a medium such as a fingertip or earlobe is very difficult to determine, since not only are optical wavelengths absorbed by the fleshy medium, but also the signals are scattered within the medium and transmitted through different path lengths. Furthermore, as indicated by the above equations, the measured signal intensity does not vary linearly with respect to the path length. Therefore, variations in path length of multiple paths of light through the medium will not result in a linear averaging of the multiple path lengths. Thus, it is often very difficult to determine an exact path length through a fingertip or earlobe. In addition to these difficulties, it has been found that there is significant difficulty in detecting glucose within water based upon Beer-Lambert's law. Specifically, it has been found that inaccurate measurements are often taken of glucose concentration within water when optical measuring instruments are calibrated so as to assume maximum transmission of optical wavelengths will occur through pure water without glucose. The present inventors have found that glucose together with water absorbs less than pure water for certain absorption bands and absorbs more for other bands.

In addition to the aforementioned difficulties, current optical spectroscopic devices, as identified by the inventors for use in the present invention, often require expensive custom-made filters which are used to generate a pattern of optical signals to be transmitted. One such filter, commonly known as a dichroic filter, comprises a rotating optically coated disk which includes regions of varying optical thickness. The regions on the dichroic filter are formed in a pattern so that rotation of the optical disk results in the transmission of selected optical bands. The high precision necessary for optically coating the filter substrate with various thicknesses of optical material on minute portions of the optical disk typically makes this coating process highly expensive. The present invention decreases the cost of a rotating dichroic filter by a factor of approximately 100 times by relaxing the specifications of the filter and compensating for the relaxation of filter specifications through more intensive signal processing steps. The filter constructed in accordance with the present invention allows from 10 to 100 times as much light to pass while maintaining the same resolution.

One aspect of the present invention involves a system for non-invasively monitoring blood glucose concentration within a patient's bloodstream. The system has a light source which emits optical radiation at a plurality of wavelengths. A receptacle receives a fleshy medium of the patient and an optical detector is positioned to receive light from the light source and attenuated by the fleshy medium. The optical detector is responsive to optical radiation of at least the plurality of wavelengths to generate an output signal indicative of the intensity of the optical radiation. A signal processor is coupled to the detector to receive the output signal. The signal processor is responsive to the output signal to isolate portions of the output signal due to optical characteristics of the fleshy medium to provide a set of frequency response values. The signal processor has a linearization module which linearizes the set of frequency response values and analyzes the linearized data to determine the concentration of glucose within the patient's bloodstream. In one embodiment, the linearization module comprises a double logarithm operation.

In one embodiment, the light source comprises a plurality of emitters, each emitter transmitting light at a selected one of the plurality of wavelengths. In another embodiment, the light source comprises a broadband light source and the system further has an optical filter which selectively passes ones of plurality of wavelengths present in the broadband light source.

In one embodiment, the detector comprises a single detector responsive to the ones of the plurality of wavelengths to provide an output signal indicative of the sum of the intensities of the ones of the plurality of wavelengths. In another embodiment, the optical detector comprises a plurality of detectors, each detector responsive to at least one of the plurality of wavelengths to generate an output signal indicative of the intensity of the at least one wavelength.

Another aspect of the present invention involves a non-invasive blood glucose monitoring system which analyzes blood glucose within a fleshy medium containing blood. The system has a light source and an optical detector responsive to light from the light source to generate an output signal. A compression device is configured to provide for physical perturbation of the fleshy medium to express fluid from the fleshy medium. A signal processor is responsive to a first output signal from the optical detector when fluid is expressed from the fleshy medium and responsive to a second output signal from the optical detector when fluid is not expressed from the fleshy medium to isolate information relating to the concentration of glucose in the blood.

Yet another aspect of the present invention involves a method of non-invasively determining blood glucose concentration. The method involves a number of steps. A set of values indicative of optical characteristics of significant blood constituents is generated and a fleshy medium having blood is illuminated with light of a plurality of wavelengths. The light is detected after attenuation of the light by the fleshy medium. A signal is generated from the detected light which is indicative of optical characteristics of the fleshy medium. Components of the signal which are indicative of the concentration of glucose in water within the blood are isolated in response to the detected light and the set of values indicative of optical characteristics of the significant blood constituents. A value is then generated indicative of the glucose concentration within the blood. In one embodiment, the significant blood constituents comprise water, hemoglobin, oxyhemoglobin and glucose dissolved in fluid.

In one embodiment, the signal is linearized to provide an indication of the concentration of blood glucose. Advantageously, the indication of the concentration does not vary significantly with respect to the path length through the medium. In one embodiment, the linearizing involves generating a first set of values indicative of the optical characteristics of the medium, taking a first logarithm of the first set of values to generate a second set of values and taking a second logarithm of the second set of values to obtain a linearized set of values that are indicative of the concentration of the blood constituent. In one embodiment, the linearization further involves transforming the first set of values using a polynomial equation to provide a transformed first set of values.

These and other aspects are described herein in further detail.

BRIEF DESCRIPTION OF THE DRAWINGS

FIGS. 4A-4C are graphs which depict the optical transmission characteristics of a dichroic filter over different degrees of rotation and at three separate wavelengths.

FIG. 4D illustrates a matrix used to specify the optical characteristics of the dichroic filter used in accordance with the present invention.

DETAILED DESCRIPTION OF THE INVENTION

OVERALL BLOOD GLUCOSE MONITORING SYSTEM

Figures 1, 2:
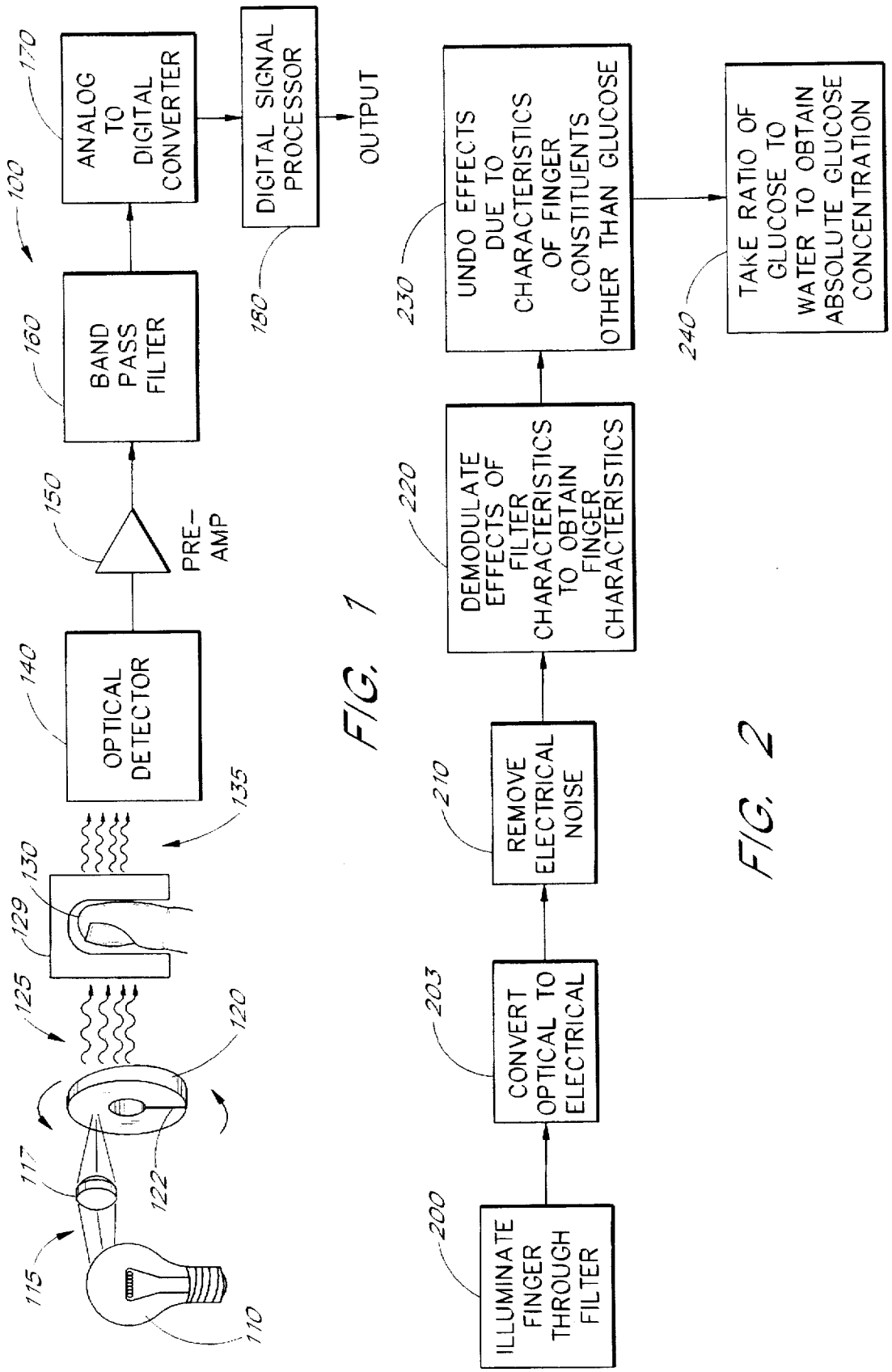
FIG. 1 is a schematic block diagram illustrating the main functional elements of the blood glucose monitoring system of the present invention.
FIG. 2 is a flow diagram which very generally depicts the method employed in accordance with the present invention to obtain blood glucose concentration.

FIG. 1 is a schematic block diagram which depicts the main functional and structural elements of a blood glucose monitoring system 100 in accordance with the present invention. As depicted in FIG. 1, the glucose monitoring system 100 includes a broadband light source 110 for emitting optical radiation 115 over a broad band of optical wavelengths. In one advantageous embodiment, the optical source 110 comprises a 3,000-kelvin, quartz, halogen lamp. In addition to the halogen lamp, the light source 110 may further comprise, in one embodiment, a first indium gallium arsenide (InGaAs) light emitting diode (LED) which emits light at a wavelength of approximately 1,300 nanometers, a second InGaAs LED which emits light at approximately 1,060 nanometers, and a third InGaAs LED which emits light at approximately 940 nanometers.

In an alternative embodiment, several LED's having wavelengths tuned to selected frequency bands could be used in place of the lamp 110. Of course, such an embodiment is typically expensive due to the cost of multiple, specifically-fabricated LED's. Thus, the preferred embodiment includes a device for producing multiple wavelengths in a cost effective manner as described below.

The optical radiation 115 emitted from the light source 110 is focused via a lens assembly 117 (which may comprise fiber optics or the like) and passes through a filtering element 120. The filter 120 may, in one advantageous embodiment, comprise a dichroic filter constructed in accordance with the teachings of the present invention, as described below with reference to FIG. 10. The dichroic filter 120 comprises an optically transmissive rotatable disk substrate which is layered with optical coatings having different thicknesses so as to modulate the broadband optical radiation 115 through a spectrum from the near infrared (NIR) (e.g., 700 nm) to the infrared (IR) (e.g., 1,400 nm). The filter 120 further includes an optically opaque strip 122 which may, for example, comprise brass or some other metal which is deposited radially outward from the center of the filter disk 120. The opaque strip provides a "0" location indicator. The filter disk 120 is driven in a circular motion (as described more fully below) by a stepper motor in one preferred embodiment. Filtered optical radiation 125 passes from the filter 120 through a fleshy medium, perfused with blood such as a finger tip 130. In some applications, it may be desirable to provide a focusing lens between the filter 120 and the finger 130.

A pressure application device 129 is shown schematically in FIG. 1 to surround the finger tip 130. As will be discussed in greater detail below, the pressure application device 129 is used to squeeze fluid out of the finger tip 130 for purposes of enhancing signal detection.

Light 135, which passes through the finger 130, is incident upon an optical detector 140. In one advantageous embodiment, the optical detector 140 comprises an InGaAs optical detector which has a well-defined optical response for wavelengths in the spectrum of interest in the preferred embodiment (e.g., between 850 and 1,700 nm).

The output of the optical detector 140 connects to a pre-amplifier 150 which advantageously comprises a class A linear amplifier having an upper dynamic limit of between 1 and 5 volts. The output of the pre-amp 150 connects to a bandpass filter 160. The bandpass filter 160 advantageously comprises a linear RC filter having a lower cut-off frequency of approximately 0.5 Hz and an upper cut-off frequency of approximately 10 kHz. The lower and upper cut-off frequencies have roll-offs of approximately 6 decibels per octave.

The bandpass filter 160 connects to an analog-to-digital converter 170, which, in one preferred embodiment comprises a Δ–Σ converter that converts the analog electrical signal output from the bandpass filter to a digital signal. The analog-to-digital convertor 170, for example, may comprise a 16-bit, 20 kHz conversion rate analog-to-digital convertor. One example is Model No. CS5317, available from Crystal Semiconductor. The digitized signal which is output from the convertor 170 is then provided to the input of a digital signal processor 180 for signal processing. In one embodiment, the digital signal processor may be implemented in software within a computer. For example, an INTEL 486 MP, or an ANALOG DEVICES DSP chip, Model No. 21062, are two examples. The digital signal processor 180 outputs a value indicative of the blood glucose level of the blood within the finger 130.

In operation, when light 115 is emitted from the broadband light source 110 over a wavelength range of approximately 700 nanometers to 1,700 nanometers, this broadband light 115 shines through the rotating dichroic filter 120. It should be noted that the light 115 is focused onto a portion of the filter 120 by means of fiber optics, a lens assembly (e.g., the lens 117), or the like. As the dichroic filter 120 rotates, the broadband light 115 is filtered through a portion of the dichroic filter 120 producing the filtered optical radiation 125. As indicated above, the dichroic filter 120 is coated with optical layers of varying thickness so that different portions of the dichroic filter 120 pass different wavelengths of light. Thus, as the filter 120 rotates, the optical radiation 125 output from the filter includes optical radiation of various wavelengths. In one embodiment, a fiber optic is used to couple the optical radiation 125 emitted from a portion of the filter 120 to the patient's finger 120. It should be noted here, that since the optical characteristics of the filter 120 can be carefully measured and the rotational speed of the dichroic filter 120 is known, the pattern of optical radiation 125 emitted from the filter 120 to illuminate the finger 130 is well defined, and therefore, may be used during signal processing to determine the amount of attenuation which is due to the optical filter 120.

The optical radiation 125 which is used to illuminate the finger 130 passes through the finger 130 to produce the detectable light 135. As is well known in the art, some of the optical radiation 125 passes unimpeded through the finger 130, some of the optical radiation 125 is reflected within the finger 130 to produce scattering. The scattered radiation which is transmitted through the finger 130, together with the light which passes unimpeded through the finger 130, make up the light 135. Some of the optical radiation 125 is absorbed by constituents within the finger 130.

The finger 130 is known to include a fingernail, skin, bones, flesh, and blood. The blood itself primarily comprises water, oxyhemoglobin, reduced hemoglobin, lipids, protein and glucose. Each of these constituents within the finger (e.g., nerves, muscle tissue, etc.) contribute to the absorption and scattering of the optical radiation 125 through the finger 130. As described above, the absorption of optical radiation through a nonhomogeneous medium typically follows well defined laws in relation to the optical characteristics of each of the constituents taken separately. These laws are expressed in the equations for Beer-Lambert's law. The light 135 which passes through the finger 130 is incident upon the optical detector 140. The optical detector 140 generates an electrical signal proportional to the overall intensity of the light 135.

Although the light 135 typically has different intensities at different wavelengths, the optical detector 140 generates an electrical signal which is proportionate to the area contained under the spectral response curve of the light 135 within the optical band detected by the detector 140. That is, the optical detector 140 receives light having different intensities at different wavelengths. The detected wavelengths are restricted over a band of approximately 850 nm to 1,700 nm due to the characteristics of the detector 140, so that, if intensity is plotted as a function of wavelength to obtain a spectral response curve, the area under the spectral response curve will be indicative of the average optical radiation intensity incident upon the detector 140. Thus, the electrical signal produced by the detector 140 is proportional to the overall (i.e., average) intensity of the light 135.

The electrical signal output by the optical detector 140 is amplified through the pre-amplifier 150 and is then passed for filtering to the bandpass filter 160. The bandpass filter 160 serves to eliminate high and low frequency noise signals which are extraneous to determining the blood glucose level within the patient. An analog signal output from the bandpass filter 160 is converted to a digital signal within the analog-to-digital converter 170. This digital signal is then transmitted to the digital signal processor 180 for processing. The method employed by the digital signal processor 180 to determine blood glucose level from the digital signal provided by the analog-to-digital converter 170 will be described in greater detail below with reference to FIGS. 3–9. Finally, a value indicative of the blood glucose level is output from the digital signal processor 180.

Figure 11:
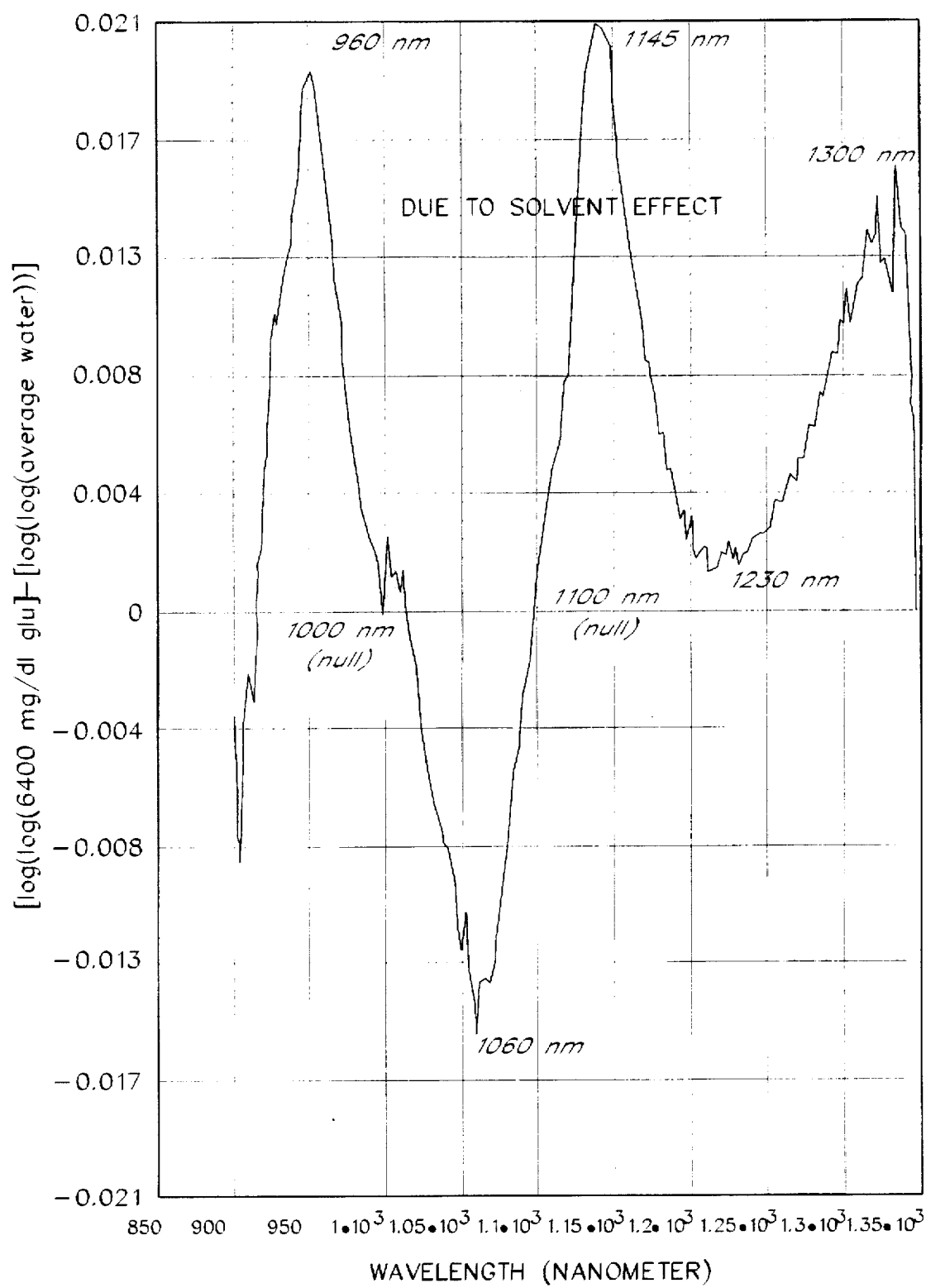
FIG. 11 is a graph which plots glucose concentrations versus wavelength with average water concentration subtracted.
Figure 12:
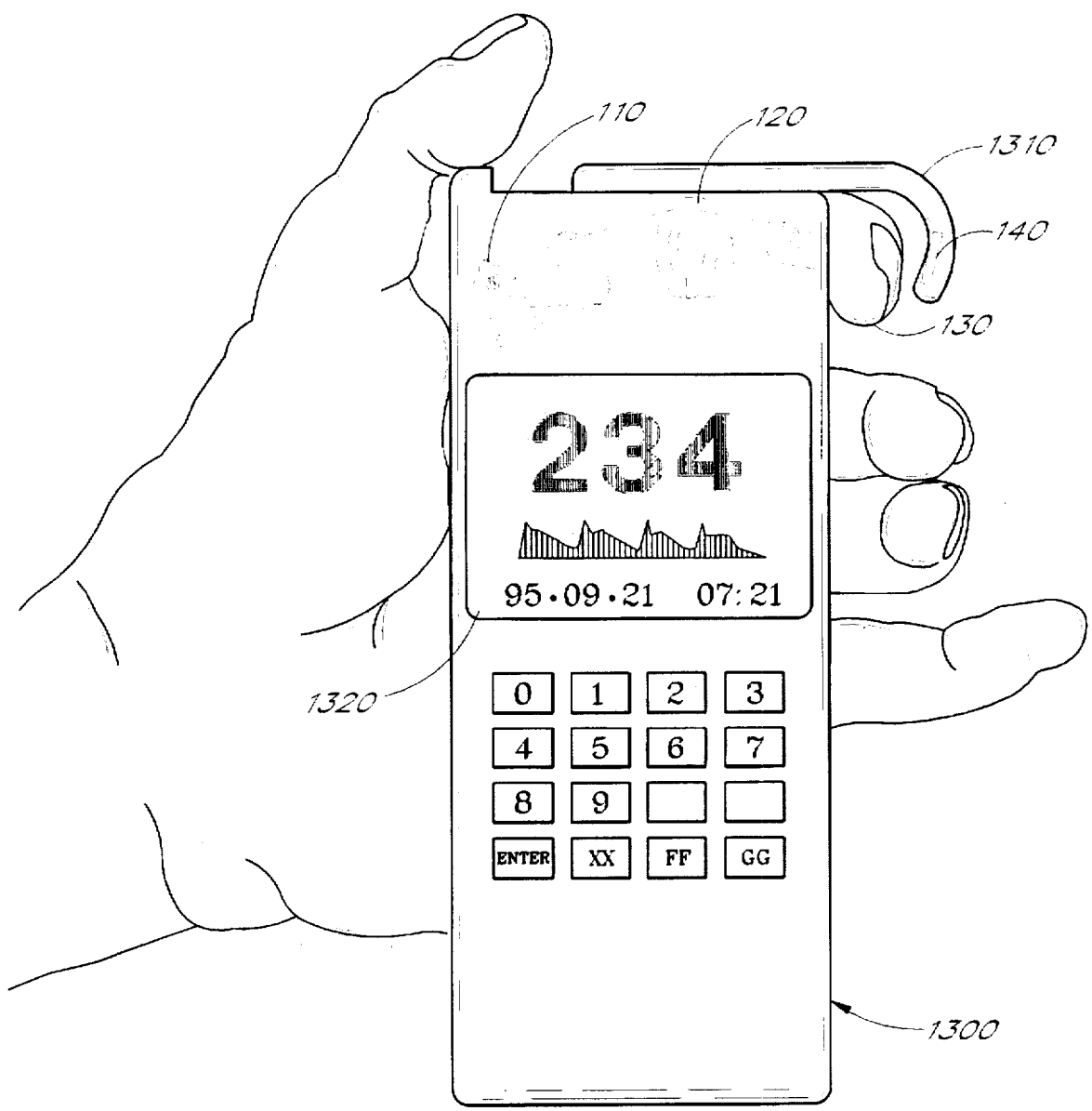
FIG. 12 schematically depicts a hand-held glucose monitor such/as may be constructed in accordance with the present invention.

It should be noted here that the signal conditioning apparatus and method used to reduce noise in the signal provided to the digital signal processor (DSP) 180 advantageously provides a very high signal-to-noise ratio (on the order of 90–100 dB, in one preferred embodiment). Such a processing system is described in pending U.S. application Ser. No. 08/320,154, entitled SIGNAL PROCESSING APPARATUS, and is hereby incorporated by reference. Particular attention is drawn to FIGS. 11, 11A, and 12, and the corresponding description of the incorporated patent application, which detail the structure and method used to obtain a signal-to-noise ratio sufficient for the application of the present invention. It should further be understood that, although the incorporated patent application is directed to an apparatus and method for obtaining blood oxygenation levels, the same signal processing steps are performed in accordance with the present invention until the 20 KHz data signal is output to the DSP as depicted in FIG. 12 of the incorporated patent.

FIG. 2 is a data flow diagram which very generally represents the overall method of signal analysis employed in accordance with the present invention to obtain the blood glucose level of a patient through noninvasive optical monitoring. First, as indicated within an activity block 200, a patient's finger 130 is illuminated by light which is filtered in a known pattern by the filter 120. The optical signal which passes through the finger 130 is converted to an electrical signal by the detector 140, as indicated within the activity block 203.

In a first analysis step, electrical noise due to the electrical components of the system 100 and ambient light incident upon the detector 140 are removed as represented by an activity block 210. Thus, for example, 60 Hz electrical noise and room light are removed in this step. Since ambient light and electrical noise is linearly mixed with the desired signal, this noise can be removed by a linear subtraction at this stage in the signal processing procedure.

Once electrical noise is removed from the electrical signal indicative of the light 135 passed through the filter 120 and the finger 130, a second analysis step is performed, as represented by an activity block 220, whereby the electrical signal is processed to demodulate the attenuation characteristics due to the filter 120. It should be understood that the filter characteristics are modulated together with the finger characteristics so that removal of the characteristics due to the filter 120 is advantageously accomplished by means of demodulation rather than linear subtraction. In this way the portion of the electrical signal due simply to the attenuation characteristics of the finger 130 is isolated.

Once the electrical signal has been processed to isolate the information solely relating to the optical attenuation characteristics of the patient's finger 130, those portions of the electrical signal which are due to the attenuative characteristics of the finger constituents other than glucose and water are extracted in a third analysis step as indicated within an activity block 230. In the preferred embodiment, a first sub-step of this third analysis step involves expressing fluids from the fingertip to leave substantially non-fluid elements of the fingertip whereby those finger constituents other than blood are extracted from the electrical signal. Another sub-step in the third analysis step involves extracting from the remaining signal representing blood those portions of the electrical signal which are due to the attenuative characteristics of blood constituents other than glucose and water. Both sub-steps are advantageously accomplished by means of demodulation to remove the signal characteristics which are not due to the glucose or water within the blood.

Finally, as represented by an activity block 240, the ratio of the concentration of glucose to the concentration of water within the patient's finger 130 is taken to extract signal characteristics due to path length through the finger 130. In this manner an absolute glucose concentration is obtained. This concentration level can be output as a value indicative of the blood glucose level of the patient.

Figure 3:
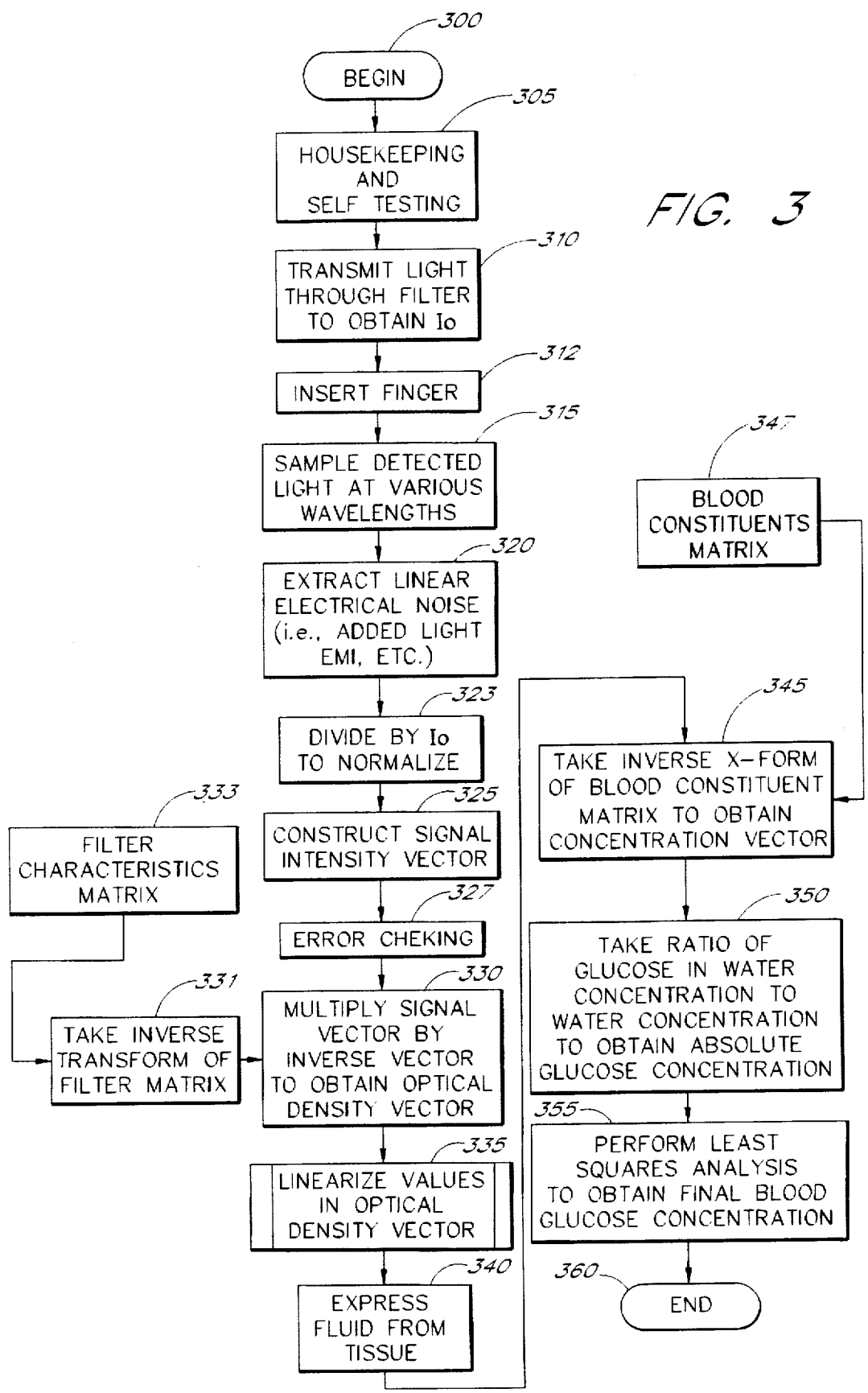
FIG. 3 is a flow diagram which illustrates in greater detail the method of the present invention used to determine blood glucose concentration within a patient.

FIG. 3 is a data flow diagram which details the method used during run-time to obtain the blood glucose level of a patient based upon detected optical signals. It should be understood, however, that prior to run-time, initialization and calibration routines other than the housekeeping and self testing procedures of block 305 are performed.

PRE-RUN-TIME INITIALIZATION

The initialization and calibration are performed at the factory or other time prior to use for patient monitor. In general, a blood constituent matrix is constructed and a filter characteristics matrix is also constructed, as described in greater detail below with reference to FIG. 7. The blood constituent matrix represents the absorption characteristics of each of the main constituents within the blood over various wavelengths of light. The filter characteristics matrix represents the absorption characteristics of the dichroic filter 120 at different portions of the filter 120 and for various wavelengths of light. The filter characteristics matrix is used in order to extract portions of the electrical signal generated by the detector 140 which are due simply to the optical attenuation caused by the filter 120. The blood constituent matrix is used for cross-correlation of light passed through tissue in order to calculate the concentration of the different constituents including glucose, water, hemoglobin, etc.

The blood constituent matrix and the filter characteristic matrix are both two-dimensional matrices. The blood constituent matrix includes one column for each constituent of blood considered and one row for each wavelength of light which is measured. In a preferred embodiment, the blood constituent matrix includes five columns and sixteen rows when five blood constituents are analyzed and sixteen wavelengths are used. The filter characteristic matrix includes one column for each wavelength of light which is measured and one row for each rotational position of the filter 120, at which an analog-to-digital sampling is performed. Thus, in one embodiment, the filter characteristics matrix includes 16 columns and 256 rows when 16 wavelengths are used and 256 rotational positions of the filter 120 are defined. It should be understood here that it is not necessary that 16 different wavelengths be used; however, the use of additional wavelengths is particularly advantageous for increasing the signal-to-noise ratio. Since about half of the incident light is transmitted through the filter at each position of the filter, the same wavelength is detected multiple times (although in a unique combination with other wavelengths each time) so that the overall signal intensity is from 10 to 100 times the intensity of any single wavelength and much higher than the noise floor. This is commonly referred to as Felgate's advantage. In this manner the spectral response of the entire filter 120 over the expected measured wavelengths is completely characterized. The method employed to construct the blood constituent matrix and the filter characteristics matrix is described in detail below with reference to FIG. 7.

RUN-TIME PROCESSING

Once initialization and calibration have been performed, the system is ready for run time use. As depicted in FIG. 3, the start of run-time processing is represented in a begin block 300. First, housekeeping and self-testing procedures are performed, as represented in an activity block 305. Briefly, housekeeping and self testing involves boot operations and ensuring proper operation of the blood glucose monitoring system 100, and to provide more accurate monitoring of the blood glucose concentration. For example, the instrument first determines if there is a sufficient signal intensity to take an accurate reading, is there a heartbeat, is the patient following instructions by pressing and releasing the finger 130, etc. After housekeeping and self testing is completed, the light source 110 is activated to transmit light 115 through the filter 120, as represented in an activity block 310. Initially, the light source 110 is activated while the patient's finger 130 is not interposed between the filter 120 and the detector 140. Thus, the light which is detected by the detector 140 represents a baseline light intensity ($I_o$) which can be used as a test to insure that a bulb which is too dim or too bright is not inserted as a replacement bulb for example.

Once the initial baseline light intensity constant has been determined, the patient inserts the finger 130, as indicated in an activity block 312, so that measurements of the blood glucose level within the patient's finger 130 may be taken. As described above, when the patient's finger 130 is inserted between the filter 120 and the detector 140, light 115 from the source 110 passes through the filter 120 and the finger 130 to be detected as light 135 incident upon the detector 140.

As indicated within an activity block 315, the light which is incident upon the detector 140 is converted to an electrical signal and this signal is amplified in the pre-amp 150, filtered with the band pass filter 160, and sampled by the analog-to-digital converter 170. Since the filter 120 is rotating (at approximately 78.125 revolutions per second in one actual embodiment, although other rotational rates could be advantageous as called for by the particular application), samples of the electrical signal output by the detector 140 are indicative of the light intensity detected at various rotational positions of the filter 120. In one advantageous embodiment, one complete rotation (i.e., 360°) of the filter 120 corresponds to 512 digital samples. That is, 512 samples are taken within the period corresponding to one revolution of the filter 120. Thus, for example, if the filter 120 rotates at 78.125 revolutions per second, then 512 samples will be taken within approximately 1/78th of a second, so that the sampling rate of the analog-to-digital converter 170 will be approximately 40,000 samples per second.

Figure 10:
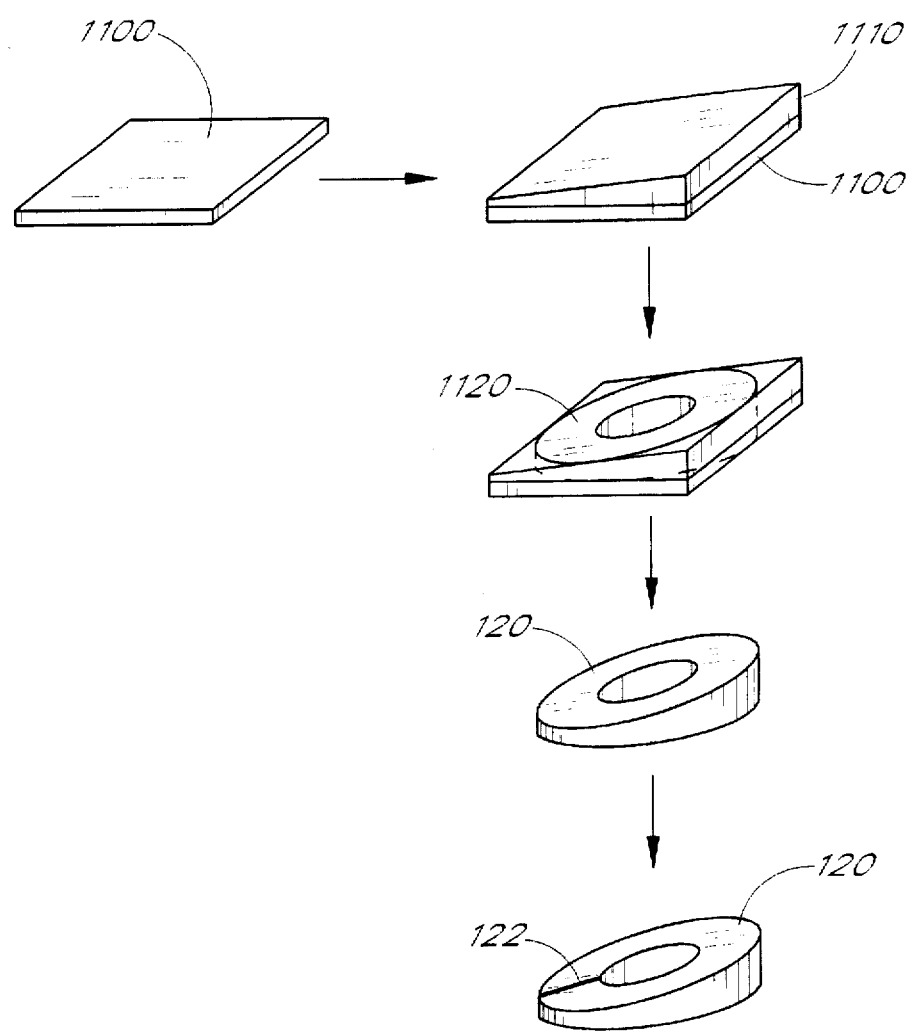
FIG. 10 depicts the method employed in accordance with the present invention to manufacture the dichroic filter depicted in FIGS. 1 and 9.

As further described below, the filter 120 constructed in accordance with the present invention includes redundant regions within an entire revolution. Specifically, the filter 120 is symmetrically layered so that the first half-revolution of the filter provides a mirror of the signal of the second half-revolution of the filter 120. That is to say, as depicted in FIG. 10, the filter is formed in a wedge shape so that the thickness in one direction is constant and the thickness in the perpendicular direction increases linearly. Thus, the second half-revolution of the filter 120 is redundant. For this reason, digital samples taken for one-half of the revolution of the filter 120 could be discarded so that in each rotation of the filter 120 there are 256 samples used for purposes of digital signal processing rather than 512 samples in the embodiment described above. Alternatively, all 512 samples can be used for processing by averaging corresponding values. In yet an alternative embodiment, the redundant half of the filter may be used for filter and source calibration. Each of the 256 samples (if only half are used) represents a different portion of the filter 120 having different optical transmission characteristics.

Once the signal output by the detector 140 has been sampled, linearly added deterministic and stochastic electrical noise inherent within the blood glucose monitoring system is extracted (i.e., linearly subtracted), as indicated by an activity block 320. The method of subtracting this noise depends upon whether the noise is deterministic or stochastic. If the noise is deterministic, then this can be modeled with the appropriate phase and subtracted. If the noise is stochastic, then the noise can be averaged towards zero. As described above, the filter 120 is specially designed to include an opaque strip (i.e., the brass strip 122). The digital signal processor 180 detects when the opaque strip 122 of the filter 120 is interposed between the light 115 and the detector 140 by monitoring the intensity output from the detector. This intensity will be effectively zero when the light is blocked by the opaque strip 122. Since the opaque strip 122 blocks substantially all of the optical radiation transmitted from the source 110, any signal output from the optical detector 140 when the light is blocked (e.g., from ambient light, thermal effects, etc.), will be interpreted as electrical noise which is not due to either the spectral absorption characteristics of the finger 130 or the spectral absorption characteristics of the filter 120. Thus, the digital signal processor 180 interprets the signal present at the output of the optical detector 140 when the brass strip 122 is interposed between the light source 110 and the optical detector 140 as stochastic noise which is subsequently subtracted from all signals output from the optical detector 140. In one embodiment, this is simply accomplished by subtracting the digital value corresponding to the detected noise level from each of the digital values corresponding to the detected signal samples obtained within the activity block 315. Alternatively, a shutter mechanism could be interposed within the light path, or the lamp 110 could be turned off momentarily to provide the same effect. In this manner, the electrical noise inherent within the blood glucose monitoring system 100 is removed so that those electrical signals due to the optical absorption characteristics of the filter 120 and of the finger 130 are considered in the further processing steps.

Once the stochastic noise inherent within the blood glucose monitoring system 100 has been extracted by averaging to zero and the deterministic noise is subtracted by phase modeling the noise or averaging the deterministic noise to zero, control of the method passes from the activity block 320 to an activity block 323. Within the activity block 323 the signal is divided by $I_o$ to normalize the signal. The normalized signal is subsequently processed within an activity block 325 to construct a signal intensity matrix, or vector, from the sample values obtained within the activity block 315 (taking into consideration the subtraction of the electrical noise performed within the activity block 320 and the signal normalization performed in the activity block 323). The signal intensity matrix is a one column matrix (sometimes referred to as a vector) including 256 signal intensity values (i.e., one value for each sampled rotational position of the filter 120). Thus, the signal intensity vector is obtained by direct measurement of the optical signal which passes through both the filter 120 and the finger 130 and is detected by the optical detector 140. Of course, the values used to form the signal intensity vector are taken from the amplitude of the signals output from the detector 140 after subtraction of the noise from each sample. Designating each rotational position of a filter 120 which is sampled by the analog-to-digital converter 170 by the symbol $\phi$, then $\phi_1$ will correspond to the first rotational position of the filter 120, $\phi_2$ will correspond to the second rotational position of the filter 120, to $\phi_{256}$, which corresponds to the last rotational position of the filter 120 before $\phi_1$ is taken again. Using this notation, $I_{\phi 1}$ corresponds to the intensity of light detected by the optical detector 140 when the filter 120 is in the first rotational position $\phi_1$, $I_{\phi 2}$ corresponds to the intensity of light detected by the detector 140 when the filter 120 is in the second rotational position $\phi_2$, etc. Thus, the signal intensity matrix comprises a single column matrix having 256 digital values from $I_{\phi 1}$ to $I_{\phi 256}$, which correspond to the optical intensities detected at each of the rotational positions of the filter 120. In one embodiment, the intensity values for several revolutions are averaged to form the signal intensity matrix.

Subsequent to the construction of the signal intensity vector within the activity block 325, error checking, or testing, is performed within an activity block 327. This test is periodically performed to insure that a valid finger sample is being monitored. Thus, at each stage of transformation and filtering, the output is examined for an expected range of values corresponding to the expected range of properties for a human finger. If the output values are found to be off-scale, then a system error occurs to indicate that the monitored sample is not valid.

Once error testing is performed on the signal intensity vector, hereinafter designated as $I(\phi)$, and the filter characteristics matrix, hereinafter designated as $F(\phi,\lambda)$, has been obtained prior to run-time, as indicated above and represented as a data input in a block 333, the signal intensity matrix together with the filter characteristics matrix may be used to obtain a matrix indicative only of the optical absorption characteristics of the finger 130, as represented in activity blocks 330, 331. That is, since the overall optical absorption characteristics of both the filter 120 and the finger 130 are known as measured within the signal intensity matrix, $I(\phi)$, and the optical absorption characteristics of the filter 120 are known as represented by the filter characteristics matrix, $F(\phi,\lambda)$ the optical absorption of the light 115 due to the characteristics of the finger 130 may be determined by removing the optical absorption due to the filter from the overall absorption of the filter 120 and the finger 130. This is accomplished by first taking the inverse transform of the filter matrix, as represented in the activity block 331, and subsequently multiplying the signal intensity vector by the inverse filter matrix, as represented in the activity block 330.

Figure 5:
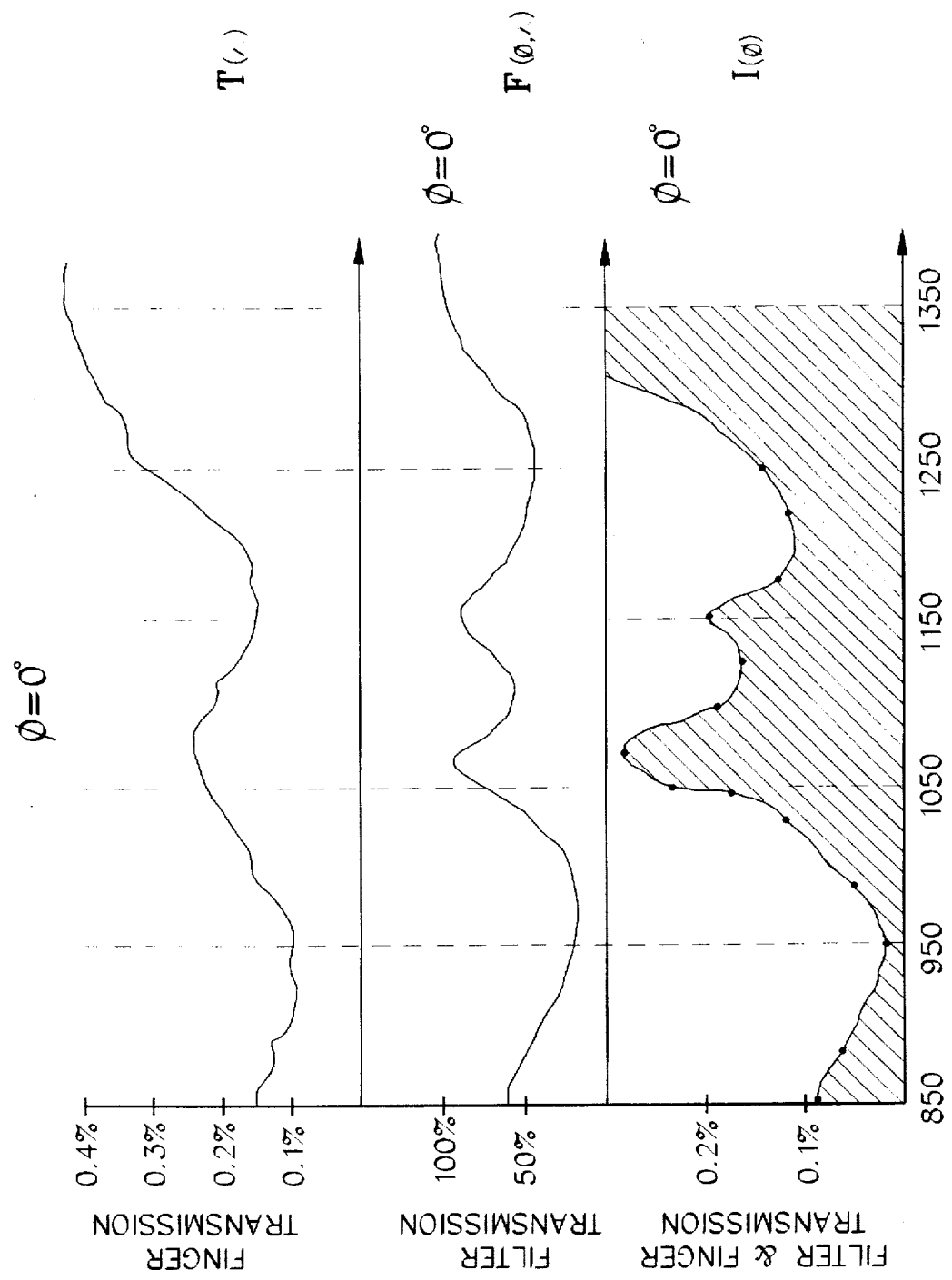
FIG. 5 depicts the optical transmicivity of a fleshy medium, such as a finger, plotted against wavelength, the optical transmicivity of a selected portion of the dichroic filter used in accordance with the present invention plotted against wavelength, and the combined optical transmicivity of the filter and the patient's finger plotted against wavelength.

FIG. 5 graphically depicts the relationship between the optical absorption due to the finger 130, the optical absorption due to the filter 120, and the total optical absorption due to both the finger 130 and the filter 120. As depicted in FIG. 5, transmission of light over wavelengths from 850 nanometers to 1,350 nanometers through the finger 130 results in a spectrum function designated as $T(\lambda)$ wherein the transmission of light through the finger 130 is plotted as a function of the wavelength. In similar fashion, the transmission of light through a selected rotational position (e.g., when $\phi=0$, corresponding to 0°) of a filter 120 is plotted as a function of wavelength and is designated by the function F(φ,λ) in FIG. 5. Finally, the combination, or convolution, of the optical absorption due to the finger 130 and the filter 120 is shown over the same wavelengths and represented in FIG. 5 by the function I(φ). To obtain I(φ) from the finger transmission function T(λ) and the filter transmission function F(φ,λ), the optical transmission percentage at any wavelength along the functions T(λ) and F(φ,λ) is multiplied to obtain I(φ). Thus, for example, at a wavelength of 1,050, the transmission of light through the finger 130 is approximately 0.24%, while the optical transmission through the filter at the same wavelength for φ=0° is approximately 80% so that the total optical transmission through both the finger 130 and the filter 120 will be approximately 0.24% times 80%, or a total of 0.192%, as indicated at the wavelength 1,050 and the function I(φ).

The functions I(φ) and F(φ,λ) may be represented by the signal intensity and filter characteristic matrices, respectively. Thus, since $$I(\phi)=F(\phi,\lambda)\times T(\lambda) \tag{3}$$

and I(φ) represents a one-column matrix (vector) containing an intensity value for each rotational position value φ, while F(φ,λ) represents a two dimensional matrix containing a filter transmission coefficient value for each value of φ and each value of λ (see FIG. 4D), then the function T(λ), representative of optical transmission through the finger 130, may be represented as a one column matrix having values for each of the various wavelength values, λ.

In accordance with one embodiment of the present invention, 16 wavelengths are selected over the range of 850 nanometers to 1,400 nanometers for purposes of characterizing the spectral characteristics of the finger 130 as well as the filter 120. Specifically, in the preferred embodiment, the monitored wavelengths are 850, 880, 910, 940, 970, 1000, 1030, 1060, 1090, 1120, 1150, 1200, 1250, 1300, 1350, and 1400 nanometers.

The matrix form of equation (3) above is shown below:

$$\begin{bmatrix} I_{\phi 1} \\ I_{\phi 2} \\ \cdot \\ \cdot \\ \cdot \\ I_{\phi m} \end{bmatrix} = \begin{bmatrix} f_{\phi 1\lambda 1} & f_{\phi 1\lambda 2} & \cdots & f_{\phi 1\lambda n} \\ b_{\phi 2\lambda 1} & \cdot & \cdots & \cdot \\ \cdot & \cdot & & \cdot \\ \cdot & \cdot & \cdots & \cdot \\ \cdot & \cdot & & \cdot \\ f_{\phi m\lambda 1} & \cdots & \cdots & f_{\phi m\lambda n} \end{bmatrix} \begin{bmatrix} t_{\lambda 1} \\ t_{\lambda 2} \\ \cdot \\ \cdot \\ \cdot \\ t_{\lambda n} \end{bmatrix} \tag{4}$$

As shown in Equation (4), the signal intensity matrix I(φ) is equal to the product of the two dimensional filter characteristic matrix, F(φ,λ), and the single column finger characteristic matrix T(λ). In this equation, two of the matrices are given (i.e., I(φ) and F(φ,λ)). Thus, the third matrix, T(λ), which represents the optical transmission characteristics of the finger 130 for the 16 selected wavelengths between 850 nanometers and 1,400 nanometers, may be obtained by simply multiplying the inverse of the filter characteristic matrix, designated as $F^{-1}(\phi,\lambda)$, by the signal intensity matrix, I(φ), using conventional matrix inversion and multiplication techniques, as shown below.

$$\begin{bmatrix} t_{\lambda 1} \\ t_{\lambda 2} \\ \cdot \\ \cdot \\ \cdot \\ t_{\lambda N} \end{bmatrix} = \begin{bmatrix} f_{\phi 1\lambda 1} & f_{\phi 2\lambda 2} & f_{\phi 1\lambda m} \\ & f_{\phi 2\lambda 1} & \cdot \\ & & \cdot \\ & & \cdot \\ & & \cdot \\ f_{\phi m\lambda 1} & \cdots & f_{\phi m\lambda n} \end{bmatrix}^{-1} \begin{bmatrix} I_{\phi 1} \\ I_{\phi 2} \\ \cdot \\ \cdot \\ \cdot \\ I_{\phi m} \end{bmatrix} \tag{5}$$

Thus, as indicated in an activity block 331, the inverse transform is taken of the filter characteristic matrix, $F^{-1}(\phi,\lambda)$, and then this inverse matrix is multiplied by the signal intensity matrix, I(φ), within the activity block 330 to obtain the frequency response of the finger 130 as expressed by the finger characteristic matrix, or transmission vector T(λ).

Once the transmission vector (or, as alternately referred to herein, the optical frequency response matrix), T(λ), has been obtained as indicated within the activity block 330, the digital values stored for each of the 16 selected wavelengths within the transmission vector are converted from a substantially logarithmic function to a linear function, as represented in a subroutine block 335. The method for converting the substantially logarithmic values stored within the transmission vector, T(λ), to linear values will be described in greater detail below with reference to FIG. 8.

LINEARIZATION OF THE TRANSMISSION VECTOR

The transmission vector, T(λ), is linearized to prevent cross modulation of interfering signals. By linearizing the transmission vector, characteristics of the detected optical signal which are not due to the optical properties of the glucose within the bloodstream can be linearly subtracted. Thus, the sequence of analysis and linearization used in accordance with the present invention is very important to prevent cross modulation of interfering signals with the desired glucose signal.

The ultimate purpose of linearizing the transmission vector, T(λ), is to eliminate path length dependent errors. As discussed above, the transmission intensity of light through a medium (e.g., such as the finger 130) has a substantially exponential relationship with the path length of the light transmitted through the medium. Thus, the different transmission characteristics vary non-linearly with the corresponding path lengths so that taking an average transmission intensity value over each of the possible transmission path lengths will not result in a transmission intensity value which is independent of path length. This is because, due to the non-linear character of the relation between the path lengths and the transmission intensity values, some path lengths are weighted more than others so that errors along the heavily weighted paths become more pronounced in the final blood glucose concentration output value. By linearizing the optical frequency response matrix, the path lengths become linearly related for each wavelength so that the path lengths can be subtracted from the set of linear equations. Once the values within the transmission vector, T(λ), have been linearized, this linearized matrix is designated by the new name D(λ) herein, which represents the optical density.

Once the values within the transmission vector have been linearized as indicated within the subroutine block 335 (FIG. 3), control of the method passes to an activity block 340, wherein, in accordance with one aspect of the present invention, significant pressure (i.e., somewhat above the patient's blood pressure) is applied to the finger tip 130 to express fluids from the finger tip 130. It should be understood that this step in the monitoring process is part of a long loop method which is not performed along with the other signal processing steps. This is because static conditions are required each time the simultaneous equations derived from the optical density vector are solved. Thus, pressure is applied to the finger for a long enough duration to derive a solution to one or more simultaneous equations, and then the finger is released for another period of time sufficient to obtain accurate solutions for additional simultaneous equations. Thus, since the application of pressure to the finger tip 130 is performed at a slower rate than the signal processing steps, the finger tip is, for practical purposes, in a static condition during each iteration of the signal processing method. Fluid is expressed from the finger tip 130 to obtain measurements of the optical characteristics of the finger not due to blood. This allows removal of portions of the electrical signal generated by the detector 140 corresponding to optical characteristics of the finger not due to the blood within the finger tip 130. Briefly, the expression of fluid within the finger tip 130 involves applying physiological pressure or other means to the patient's finger 130 and releasing the pressure so as to cause substantially all of the blood to evacuate the finger 130. As is known in the art, the finger 130 contains not only blood, but also bone, flesh, skin and nail, all of which absorb optical radiation, and therefore, contribute to the absorption characteristics defined within the transmission vector. However, for purposes of the present invention, it is not useful to include the optical absorption characteristics of bone, flesh or other non-blood constituents of the finger 130 for calculating blood glucose; these finger constituents may be considered as artifacts which should be extracted from the data used to determine blood glucose levels.

In order to remove these artifacts due to non-blood constituents of the finger 130, significant pressure is applied to the finger tip 130. When the finger 130 is physiologically altered so as to cause blood to flow in and out of the finger tip 130, the optical transmission characteristics of the finger tip 130 when the blood is evacuated from the finger tip 130 differs from the optical transmission characteristics of the fingertip 130 when blood flows into the fingertip 130. The difference is effectively the optical transmission characteristics of the blood, and other fluid, which was evacuated. Stated another way, the optical characteristics of the fingertip 130 which is full of blood is a combination of the optical transmission characteristics of the fingertip 130 when the blood is evacuated, and the optical transmission characteristics of the evacuated blood. Thus, by subtracting the signal produced by the optical detector 140 when blood is evacuated from the finger from the signal produced by the optical detector 140 when the finger is full of blood, the optical transmission characteristics of the evacuated blood may be obtained. It will be understood by this description that the blood need not be completely evacuated. In this manner, artifacts due to bone, flesh, nail and skin of the fingertip 130 are removed, or extracted, from the digitally processed signal generated by the optical detector 140. It should further be noted that other methods to express blood from the finger tip 130 may include, for example, raising the patient's arm in the air so that gravity causes a decrease in the flow of blood in the finger 130.

FIG. 12 depicts an exemplary embodiment of a device which could be used to provide for expression of fluids from the fingertip 130 during spectral analysis in accordance with the present invention. As shown in FIG. 12, a hand-held glucose monitor 1300 includes the light source 110, the lens 117, the dichroic filter 120, and the detector 140 (all shown in phantom). The fingertip 130 is placed between a caliper pressure arm 1310 which may be used to apply pressure to the fingertip 130. A display 1320, which displays glucose concentration, is also shown in FIG. 12.

In a particularly advantageous embodiment, a pronounced perturbation of the fingertip 130 may be performed in order to obtain additional information regarding the optical characteristics of the fingertip 130 and the blood therein. In such an embodiment, the fingertip could be placed within an inflatable jacket which is inflated to a relatively high pressure to squeeze most of the blood out of the fingertip 130. Thus, nearly 100% modulation of the signal due to the blood flow in the fingertip 130 is achieved in this manner. This high modulation increases the signal-to-noise ratio of the electrical signal due to the blood in the fingertip 130. Of course, it should be noted that such high modulation may change the path length through the fingertip medium (since the thickness of the finger may be significantly altered). Such a change in path length may require compensation.

For this reason, in one embodiment of the invention, a second water coefficient value is included in the blood constituents matrix, hereinafter designated as $A(\lambda,r)$, where r designates the number of blood constituents which are used to form the blood constituent matrix. This second water coefficient value may be used to determine the change in the "depth" of water through the fingertip when there is significant modulation of the fingertip. Thus, a first water depth is calculated using a first coefficient at one time when the finger is not squeezed, while a second water depth is calculated using the second coefficient at another time when the finger is squeezed. The change of the depth of the water in the fingertip is substantially the same as the change in path length through the finger, so that the change in water depth may be taken to be representative of the change in path length. Thus, by using first and second coefficients for water in the finger 130 at selected intervals, a ratio may be obtained which is indicative of the ratio between the path length through the finger 130 with modulation and the path length through the finger 130 without modulation.

Once the signal features due to the non-blood artifacts within the fingertip 130 are extracted, those optical characteristics which are due to the blood constituents other than glucose and water are extracted from the optical signal, as represented in an activity block 345. The blood glucose concentration level within the water of the blood stream is then determined, as further explained.

As indicated within the activity block 345, a concentration matrix is derived from the linearized finger frequency response characteristic matrix, $D(\lambda)$, (after extraction of non-blood signal features) and the blood constituent matrix, $A(\lambda,r)$. The blood constituent matrix is provided as a data input to the process performed within the activity block 345, as indicated within the block 347. As is well known in the art, and discussed briefly above, when several substances are combined to form a medium with optical absorption, the overall optical absorption and transmission characteristics of the combined medium are typically describable in terms of the optical characteristics of each of the separate constituents of which the medium is composed. Thus, for example, if a medium is composed of water, oil, and alcohol (which are only used here for illustrative purposes, since, in practice, these elements are insoluble), the optical transmission through the entire medium may be described, in accordance with Beer-Lambert's law, as proportional to the sum of the exponents of the optical absorption characteristics of the first constituent (i.e., water) times a concentration of the first constituent times the path length through the medium; plus the optical absorption coefficient of the second constituent (i.e., oil) times the concentration of the second constituent times the path lengths through the medium plus the absorption coefficient of the third constituent (i.e., alcohol) times the concentration of the third constituent times the path length through the medium. That is, $$I = I_o e^{[\alpha_w \cdot C_w \cdot P1 + \alpha_o \cdot C_o \cdot P1 + \alpha_A \cdot C_A \cdot P1]} \quad (6)$$

Since the optical absorption coefficient for each material typically varies as a function of wave length, a series of equations may be derived to describe the overall optical absorption characteristics of the entire medium as a function of the constituents of that medium. Thus, $$I_{\lambda 1} = I_o e^{[\alpha_{1w} \cdot C_w \cdot P1 + \alpha_{1o} \cdot C_o \cdot P1 + \alpha_{1A} \cdot C_A \cdot P1]} \quad (7)$$

$$I_{\lambda 2} = I_o e^{[\alpha_{2w} \cdot C_w \cdot P1 + \alpha_{2o} \cdot C_o \cdot P1 + \alpha_{2A} \cdot C_A \cdot P1]}$$

$$\vdots$$

$$I_{\lambda N} = I_o e^{[\alpha_{Nw} \cdot C_w \cdot P1 + \alpha_{No} \cdot C_o \cdot P1 + \alpha_{NA} \cdot C_A \cdot P1]}$$

Dividing both sides by $I_0$ and taking the logarithm of each side provides the following equation:

$$\ln\left(\frac{I_{\lambda 1}}{I_o}\right) = \alpha_{1w} \cdot C_w \cdot P1 + \alpha_{1o} \cdot C_o \cdot P1 + \alpha_{1A} \cdot C_A \cdot P1 \quad (8)$$

for the first wavelength $\lambda_1$, for example. If the optical transmission through the blood constituents perfectly followed Beer-Lambert's law, then a first logarithm would result in a set of linear equations as shown above. From these equations, simple matrix algebra could be used to obtain the concentration of glucose in blood. However, as will be discussed in greater detail below, the optical characteristics of multiple constituents within the bloodstream do not result in a set of linear equations after taking a single logarithm. Thus, the present invention contemplates a different approach which includes the steps of taking a near-log of the values within the transmission vector, followed by two true logarithms, or another near-log in an alternative embodiment, to obtain more precise linearization of the transmission vector. It should be understood that preliminary linearization and other correction steps are used in conjunction with the above steps to insure that the conditions of Beer-Lambert's law are satisfied before either logarithm is taken. Furthermore, it may not be necessary to perform the second logarithm if a sufficiently linear outcome is observed after the first logarithm is taken.

The double logarithm process is used in accordance with the teachings of the present invention to arrive at a series of linear equations which may be described in matrix form. This linearization takes place within the subroutine block 335 and is described in greater detail below with reference to FIG. 8.

The transmission vector, $T(\lambda)$, is now designated as a single column linearized finger spectrum matrix, $D(\lambda)$. Thus, for each of the 16 selected wavelengths of light, there exists a digital value corresponding to the linearized optical frequency response matrix, $D(\lambda)$. That is, $D(\lambda)$ comprises a first value $D_{\lambda 1}$ indicating the linearized absorption coefficient for the finger tip 130 at wavelength $\lambda_1$, $D_{\lambda 2}$ indicating the linearized attenuation coefficient for the finger tip 130 at wavelength $\lambda_2$, etc., to $D_{\lambda n}$.

As discussed earlier, the above Beer-Lambert equations are typically not an accurate expression of the relation between the signal intensity values and the concentration values. Thus, linearization of the transmission vector involves a "double-logarithmic" curve-fit process. The double logarithmic process need only be carried out on the transmission vector, however, and does not need to be carried out on the blood constituent matrix and the concentration vector to obtain a set of linear equations. Thus, each linearized signal strength value, $D_\lambda$, is modeled by the absorption coefficient times the path length times the concentration of each of the constituents within the blood. The linearized signal strength matrix, $D(\lambda)$, may be expressed as a product of the blood constituent matrix, $A(\lambda,r)$, and the concentration times path length matrix, hereinafter designated as $C(r)PL$. This representation is shown in matrix form as:

$$\overbrace{\begin{bmatrix} D\lambda_1 \\ D\lambda_2 \\ \vdots \\ D\lambda_N \end{bmatrix}}^{D(\lambda)} = \overbrace{\begin{bmatrix} a11 & a12 & \cdots & a1r \\ a21 & a22 & & \\ \vdots & & & \vdots \\ an1 & \cdots & \cdots & anr \end{bmatrix}}^{A(\lambda,r)} \overbrace{\begin{bmatrix} c_1 PL \\ c_2 PL \\ \vdots \\ c_r PL \end{bmatrix}}^{C(r) \cdot PL} \quad (9)$$

where PL represents the path length and $c_1, c_2, \ldots, c_r$ represent the concentration of the first blood constituent, the second blood constituent, ..., and the last blood constituent (designated by "r"). In accordance with well known matrix algebra techniques, the matrix representing the concentration times path length matrix, $C(r)PL$, may be determined by taking the product of the linearized optical frequency response matrix, $D(\lambda)$, and the inverse of the blood constituent matrix, $A(\lambda,r)$, as depicted below.

$$\overbrace{\begin{bmatrix} c_1 PL \\ c_2 PL \\ \vdots \\ c_r PL \end{bmatrix}}^{C(r) \cdot PL} = \overbrace{\begin{bmatrix} D\lambda_1 \\ D\lambda_2 \\ \vdots \\ D\lambda_N \end{bmatrix}}^{D(\lambda)} \cdot \overbrace{\begin{bmatrix} a11 & a12 & \cdots & a1r \\ a21 & a22 & & \\ \vdots & & & \vdots \\ an1 & \cdots & \cdots & anr \end{bmatrix}^{-1}}^{A^{-1}(\lambda,r)} \quad (10)$$

As indicated within the activity block 345, the inverse transform, $A^{-1}(\lambda,r)$, of the blood constituent matrix together with the linearized optical frequency response matrix may be used to obtain a matrix indicative of the concentration of the different constituents within the patient's blood.

Once a matrix indicative of the concentration of the different blood constituents has been derived as indicated within the activity block 345, the ratio of glucose concentration times path length through the finger 130 to water concentration times path length through the finger 130 is calculated as indicated within an activity block 350. This ratio is the concentration of glucose in water which is the same as the glucose concentration within the blood stream. The above described method is performed over several iterations so that several glucose concentration values are obtained. To obtain an average glucose concentration value, least squares analysis, which is well known to those skilled in the art, is used to plot a line indicative of blood glucose concentration as indicated within an activity block 355. This value is output to a display (see FIG. 12) which may be read by the patient or by the operator of the blood glucose monitor system 100. Control of the method then passes from the activity block 355 to an end block 360 wherein the method of the present invention is completed.

DERIVATION OF THE FILTER CHARACTERISTIC AND BLOOD CONSTITUENT MATRICES

Figure 7:
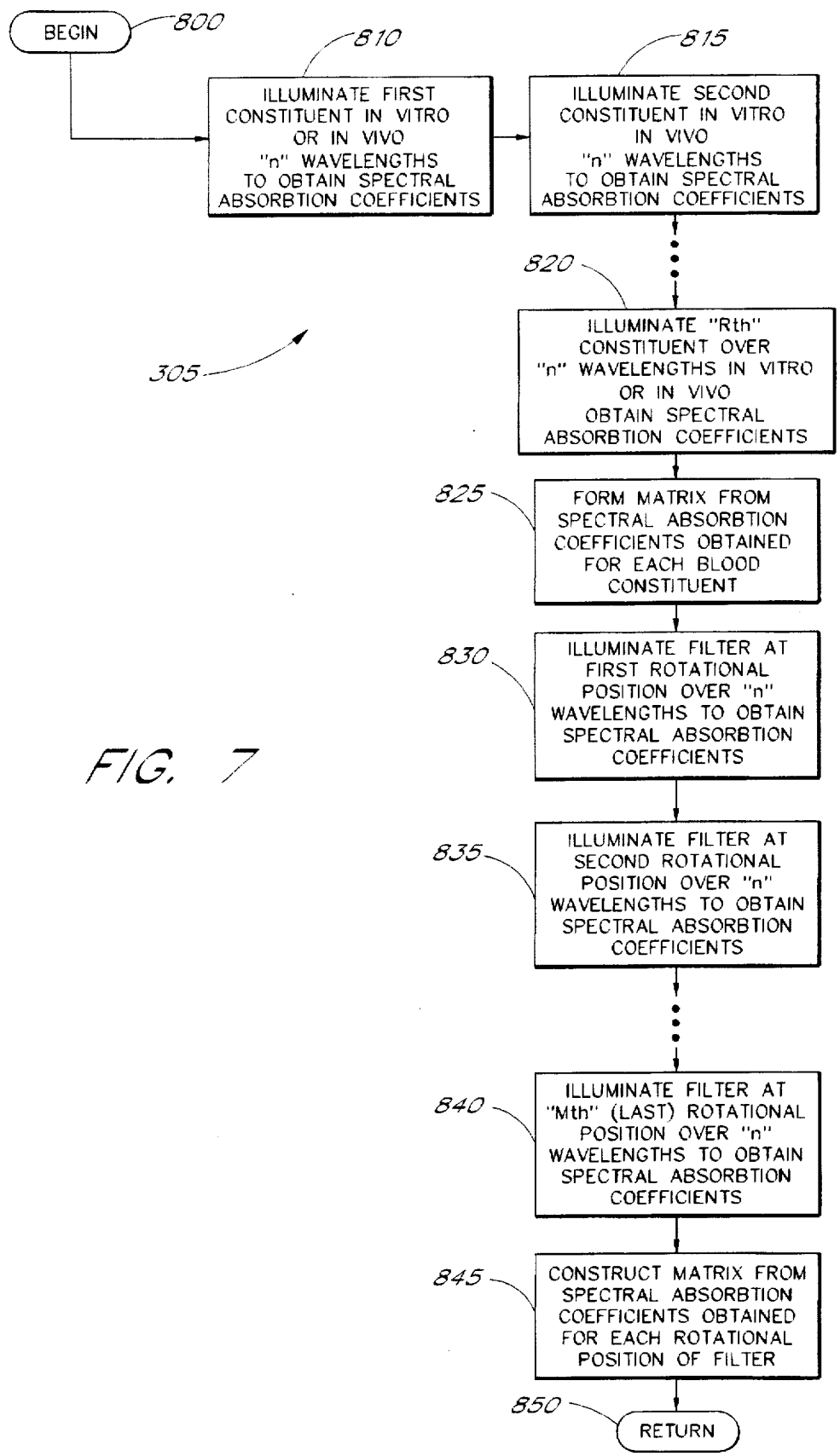
FIG. 7 is a flowchart which depicts the method used in accordance with the present invention to perform initialization and calibration functions.

FIGS. 4A–4D, together with FIG. 7, illustrate in greater detail, the method employed in accordance with the present invention to perform pre-run-time initialization and calibration of the blood glucose monitoring system 100. The initialization and calibration routine is illustrated in FIG. 7 and starts with a begin block 800. Control passes from the begin block 800 to an activity block 810.

Activity blocks 810–825 illustrate the method employed in accordance with the present invention to obtain the blood constituent matrix, $A(\lambda, r)$, while activity blocks 830–845 illustrate the method used to obtain the filter characteristics matrix. It should be understood, however, that although the method depicted in FIG. 7 is represented as though the blood constituent matrix is constructed followed by the filter characteristics matrix, in practice these represent independent procedures which may be run in parallel.

As discussed above, different substances typically have different spectral characteristics. That is, different substances absorb light more or less across different wavelengths of light. Thus, when the optical transmission of light is plotted versus wavelengths for a given substance, a pattern, which is sometimes referred to as the spectral signature of a substance, is observed. This signature defines the spectral characteristics of the substance over the various wavelengths of light.

To form the blood constituents matrix, $A(\phi, \lambda)$, the main constituents of blood are separated into individual substances, and the spectral characteristics of these substances are plotted versus wavelength. Separation of the individual substances may be performed by an actual physical separation of the constituents in vitro or by means of an in vivo clinical test wherein the concentrations of the individual substances are carefully controlled to provide a reference for monitoring the concentrations of the various blood constituents. In the present embodiment, since 16 wavelengths between 850 nanometers and 1,400 nanometers are used to characterize the optical characteristics of the patient's finger 130, the same 16 wavelengths are used in order to construct the blood constituents matrix. Thus, for each substance or main constituent within the blood, a measurement is taken to obtain the absorption at each of the 16 wavelengths.

Each of these 16 values, which are referred to as spectral absorption coefficients, is used to define a row of the blood constituents matrix, $A(\phi, \lambda)$. Likewise, each column of the blood constituents matrix will correspond to a particular blood constituent so that there is the same number of columns in the blood constituents matrix as there are blood constituents. Thus, if there are "r" constituents of blood and "n" wavelengths over which the optical characteristics of these constituents are to be determined, the blood constituents matrix comprises an "n" row by "r" column matrix.

As indicated within the activity block 810, for the cases of blood constituents that can be physically separated, the first constituent (e.g., water) is illuminated as a separate substance over the n wavelengths of light (i.e., in this embodiment, 16 wavelengths) to obtain the spectral absorption coefficients of water over these end wavelengths. For example, a calibration sample could be used in this case. Then, as indicated in an activity block 815, the second constituent of blood is illuminated with the n wavelengths of light to obtain the spectral absorption coefficients of the second constituent (e.g., oxyhemoglobin). This is repeated for each of the main blood constituents until the "rth" blood constituent (e.g., glucose in water) is illuminated over the n wavelengths to obtain the spectral absorption coefficients of the last main blood constituent.

In a preferred embodiment, certain constituents, such as water and glucose dissolved in water, are measured in vitro, while other blood constituents, such as oxyhemoglobin and deoxyhemoglobin, are preferably measured in vivo due to the difficulty of obtaining accurate in vitro measurements for these constituents. Furthermore, it should be noted that in a non-imaging system, such as typically used to perform in vivo measurements, the source and the detector should be diffuse. The in vivo and in vitro measurements are used as an approximation, and an iterative process is used with the approximate values until the linearization process described above converges. In this manner, n (e.g., 16 in the present embodiment) absorption coefficient values are obtained for each of the r constituents. In accordance with preferred embodiment of the present invention the spectral characteristics for glucose, water, oxyhemoglobin and deoxyhemoglobin as separate substances are determined. In addition, a fifth "constituent" row within the blood constituent matrix is defined by absorption coefficients of blood due to scattering. A further sixth constituent row may be added where the sixth constituent is water again. This additional constituent may be used to double check the path lengths obtained at different times during, for example, application of significant physiological pressure to the fleshy medium.

As is well known in the art, the transmission of optical radiation through a medium typically involves the scattering and reflection of light waves through the medium. This scattering effectively increases the path length through the medium. Since some of the effects due to scattering are statistically well defined, the extinction effects due to scattering may be treated as an additional constituent within the bloodstream. The "absorption" coefficients for the scattering "constituent" may be determined empirically by transmitting light through an optical medium of which the concentrations of each of the constituents is already known.

Once all the main blood constituents have been defined over the wavelengths of interest for each of the 16 wavelengths from 850 nanometers to 1,400 nanometers, the blood constituents matrix is formed from the spectral absorption coefficients obtained for each blood constituent. Thus, the first column of the blood constituent matrix has each of the absorption coefficients for wavelengths $\lambda 1, \lambda 2,$ to $\lambda n$, for the first blood constituent (e.g., water). The second column of the blood constituent matrix has the absorption coefficient values for each of the wavelengths $\lambda 1, \lambda 2,$ to $\lambda n$, for the second blood constituent (e.g., oxyhemoglobin). And so on until the last column of the blood constituent matrix comprises the spectral absorption coefficients for the last main blood constituent at the selected wavelengths $\lambda 1, \lambda 2, \ldots \lambda n$.

The activity blocks 830–845, together with FIGS. 4A–4D, illustrate the method used in accordance with the present invention to construct the filter characteristics matrix. As discussed above, the filter 120 reflects and transmits optical radiation in different proportions for different wavelengths at different places on the filter disk 120. This is clearly illustrated in FIG. 4A–4C, wherein FIG. 4A represents the optical transmission of light at a wavelength of 850 nanometers plotted versus each of a possible 256 disk rotational positions. As shown in FIG. 4A, when the disk 120 is in the initial starting position (i.e., $\phi=0$), the transmission of light at 850 nanometers is approximately 10% through the filter 120, while when the disk 120 is rotated so that $\phi=32$, the optical transmission of light at 850 nanometers through the filter 120 is approximately 25%. Again, between the disk rotational positions of $\phi=128$ to $\phi=160$, the transmission of light at 850 nanometers wavelength through the filter 120 is approximately 75%. Thus, the optical transmission for $\lambda=850$ nanometers is entirely characterized over 256 rotational positions of the disk filter 120, as depicted in FIG. 4A.

FIG. 4B depicts the optical transmission characteristics of light at 1,150 nanometers over the same 256 rotational positions of the disk 120. Similarly, FIG. 4C depicts a plot of the optical transmission of light at 1,350 nanometers through the disk filter 120 at each of the 256 rotational positions of the disk 120. In one actual embodiment of the invention, the optical transmission characteristics of the filter 120 are described for 256 rotational positions at each of 16 wavelengths between 850 nanometers and 1,400 nanometers.

Thus, from these measurements, a filter characteristic matrix may be constructed, as shown in FIG. 4D. The filter characteristic matrix designated in FIG. 4D as $F(\phi,\lambda)$ includes 256 rows and 16 columns. Each column of the filter characteristic matrix comprises the spectral absorption characteristics of the disk 120 at each of the 256 rotational positions of the disk 120 for a given wavelength.

In order to construct the filter characteristic matrix depicted in FIG. 4D, the filter 120 is illuminated at a first rotational position over each of the 16 wavelengths to obtain spectral absorption coefficients for each of the 16 wavelengths, as indicated within an activity block 830. Once the spectral absorption coefficients have been determined for the first rotational position as indicated within the activity block 830, the filter is illuminated at a second rotational position (i.e., $\phi=1$) over the 16 selected wavelengths to obtain spectral absorption coefficients for the second rotational position, as represented in an activity block 835. This method is carried on for each of the possible rotational positions of the disk 120 until, as indicated within an activity block 840, the filter is illuminated at the "mth," or last, rotational position (i.e., position 256) of the disk filter 120 over the 16 selected wavelengths to obtain the spectral absorption coefficients for the last rotational position. In one preferred embodiment, where a stepper motor is used, the rotational positions will be precise from revolution to revolution of the disk 120. Of course, a computer disc motor with salient poles and run at a constant speed could be used provided that phase dithers are minimized to less than one part in 256.

Once spectral absorption coefficients have been determined for all 16 wavelengths of all 256 rotational positions of the disk 120, the filter characteristics matrix is constructed, as indicated within an activity block 845 by putting coefficients corresponding to various blood constituents in rows and wavelengths of the transmitted light in columns. Once the filter characteristics matrix and blood constituent matrix are constructed, the system has the necessary constraints for routine processing.

The Solvent Effect

Although it is typically the case that when several substances are mixed to form constituent elements of an optical medium, the optical transmission and absorption characteristics of the medium relate to the optical transmission and absorption characteristics of each of the constituent elements within the medium as described by Beer-Lambert's law, it has been found that in certain isolated cases, this is not the case. In particular, when glucose is mixed in water so as to dissolve in water, the optical characteristics of the combination of glucose and water do not correlate directly to the optical characteristics of glucose and water separately in accordance with the relation described by Beer-Lambert's law. In fact, when glucose is dissolved into water, it is found that the glucose water solution has a lower absorptivity (i.e., a higher transmicivity) than water without glucose at certain wavelengths.

In past systems which monitor blood glucose concentration by means of optical signal detection and processing, this solvent effect, which was heretofore unrecognized in applications involving blood spectroscopy, was the cause of a significant amount of inaccuracy and detection of the actual blood glucose concentration. Thus, in accordance with the teachings of the present invention, special modifications are made to both the blood constituent matrix, $A(\lambda,r)$, and the filter characteristic matrix, $F(\phi,\lambda)$ in order to compensate for inaccuracies and non-linearities due to the solvent effect.

Specifically, the blood constituents matrix includes absorption coefficients for glucose as dissolved in water, rather than glucose as a separate substance. The scale factor by which the absorption coefficients for glucose dissolved in water differs from the absorption coefficient of water is approximately equal to $\log(-\log T_{wg})-\log(-\log T_w)$, where $T_{wg}$ is the transmicivity of water having glucose dissolved therein, and $T_w$ is the transmicivity of pure water.

Furthermore, the wavelengths which are to be monitored (which defines the filter characteristics matrix) are selected differently than would be expected for a glucose/water mixture. This is because the solvent effect causes a small shifting in the frequencies of maximum absorption of the blood constituents. For example, glucose and water acting as separate agents would have respective wavelength absorption maxima at approximately 1070 nanometers and 975 nanometers. However, due to the solvent effect, the water with glucose has one absorption maximum at approximately 960 nanometers.

Since the absorption characteristics of pure water differ from the absorption characteristics of water having dissolved glucose as a function of wavelength, this difference in absorption characteristics may be used to scale absorption coefficient values for glucose dissolved in water within the bloodstream. FIG. 11 represents the ratio between the optical absorption characteristics of water and water with glucose. As shown in FIG. 11, water containing dissolved glucose has substantially lower absorption than pure water at approximately 960 nanometers, 1145 nanometers, and 1380 nanometers, while pure water has substantially lower absorption than water containing dissolved glucose at approximately 1060 nanometers, and substantially the same absorptivity is observed for both at wavelengths of 1000 nanometers, 1100 nanometers, and 1230 nanometers. It should be noted that those values of the curve of FIG. 11 within the shaded region are due to the solvent effect, and are therefore unexpected in normal spectroscopy applications. The values of the difference between the absorptivities of pure water and water with glucose at the peak wavelengths (i.e., 960, 1060, 1145, etc.) vary as a function of glucose concentration. By using the wavelengths for which the absorptivity is substantially the same for both pure water and water with glucose as a baseline, scaling factors for determining the absorption coefficients of glucose dissolved in water may be determined. Thus, the present invention provides for more accurate measurement of the blood glucose level due to recognition of the solvent effect, and increased sensitivity if one uses 1060 nm wavelength (i.e., the minimum) to provide an increased difference value with the 960 nm and 1145 nm wavelengths (i.e., the maximum).

Method for Linearizing the Optical Frequency Response Matrix

Figure 6A:
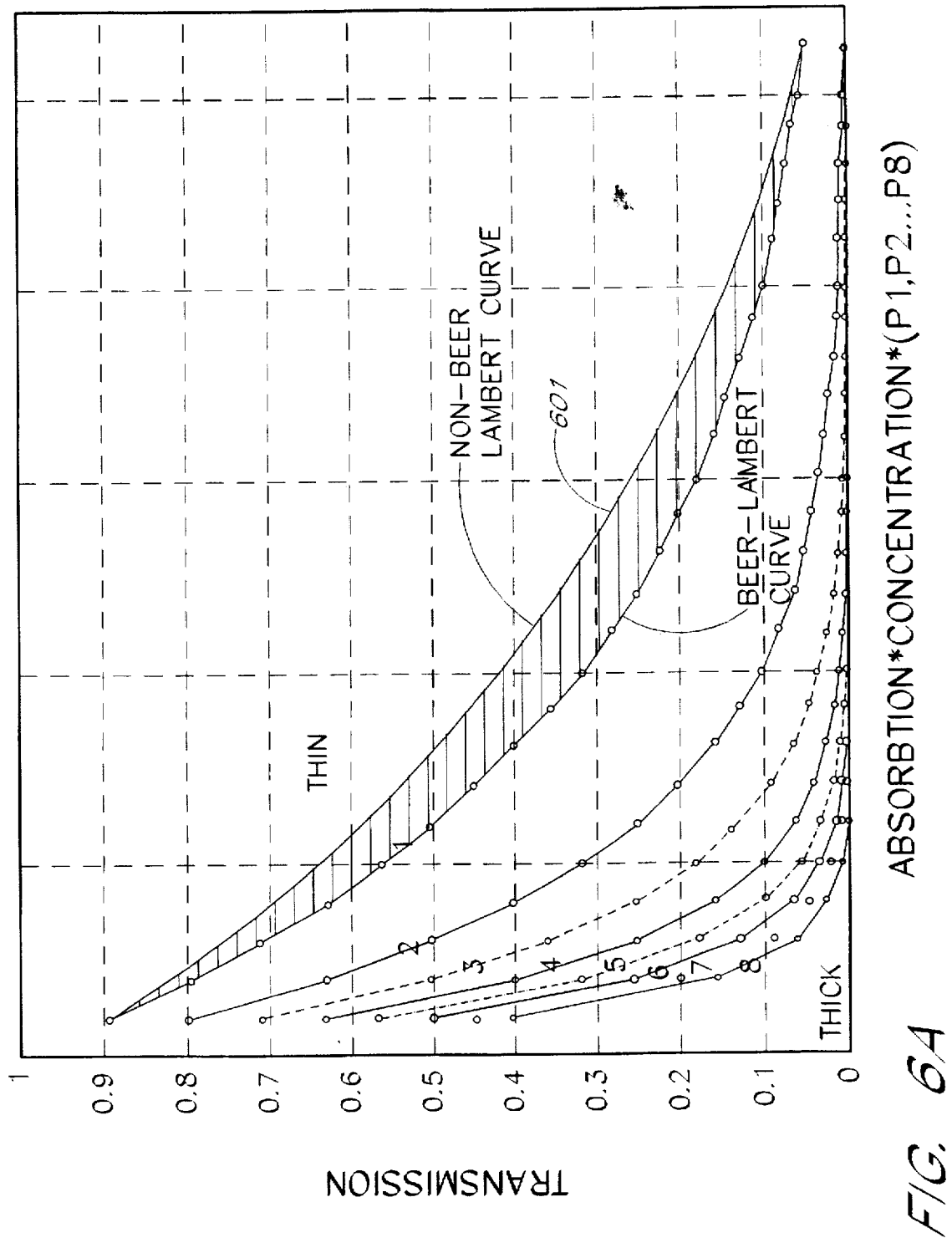
FIG. 6A illustrates a plot of optical transmission through a medium versus a product of the absorption coefficient associated with the medium, the concentration of a substance within the medium, and the path length through the medium.
Figure 6B:
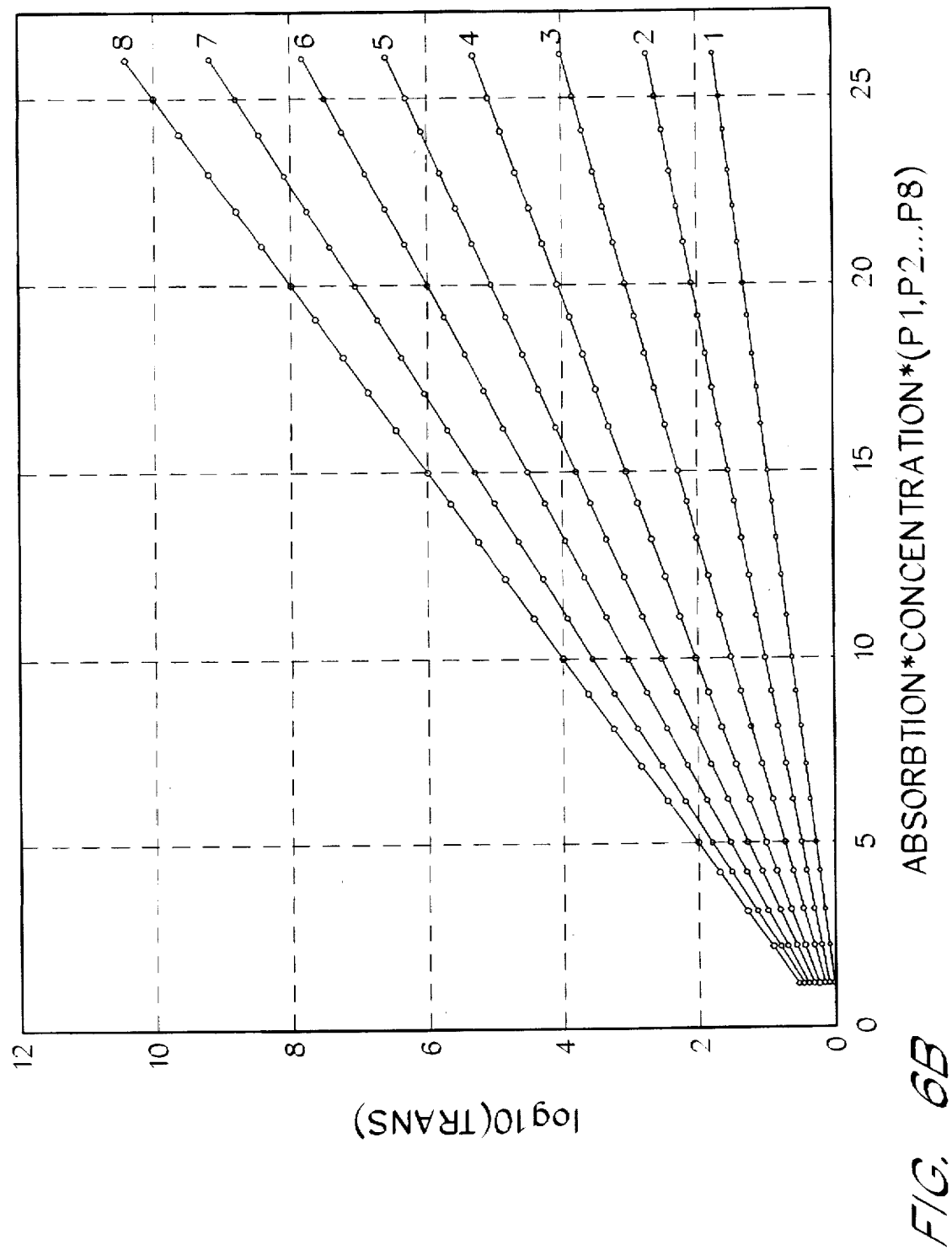
FIG. 6B is a plot of a "near-log" of the transmission through an optical medium versus a product of the absorption coefficient associated with the medium, the concentration of the substance within the medium, and the path length through the medium.
Figure 6C:
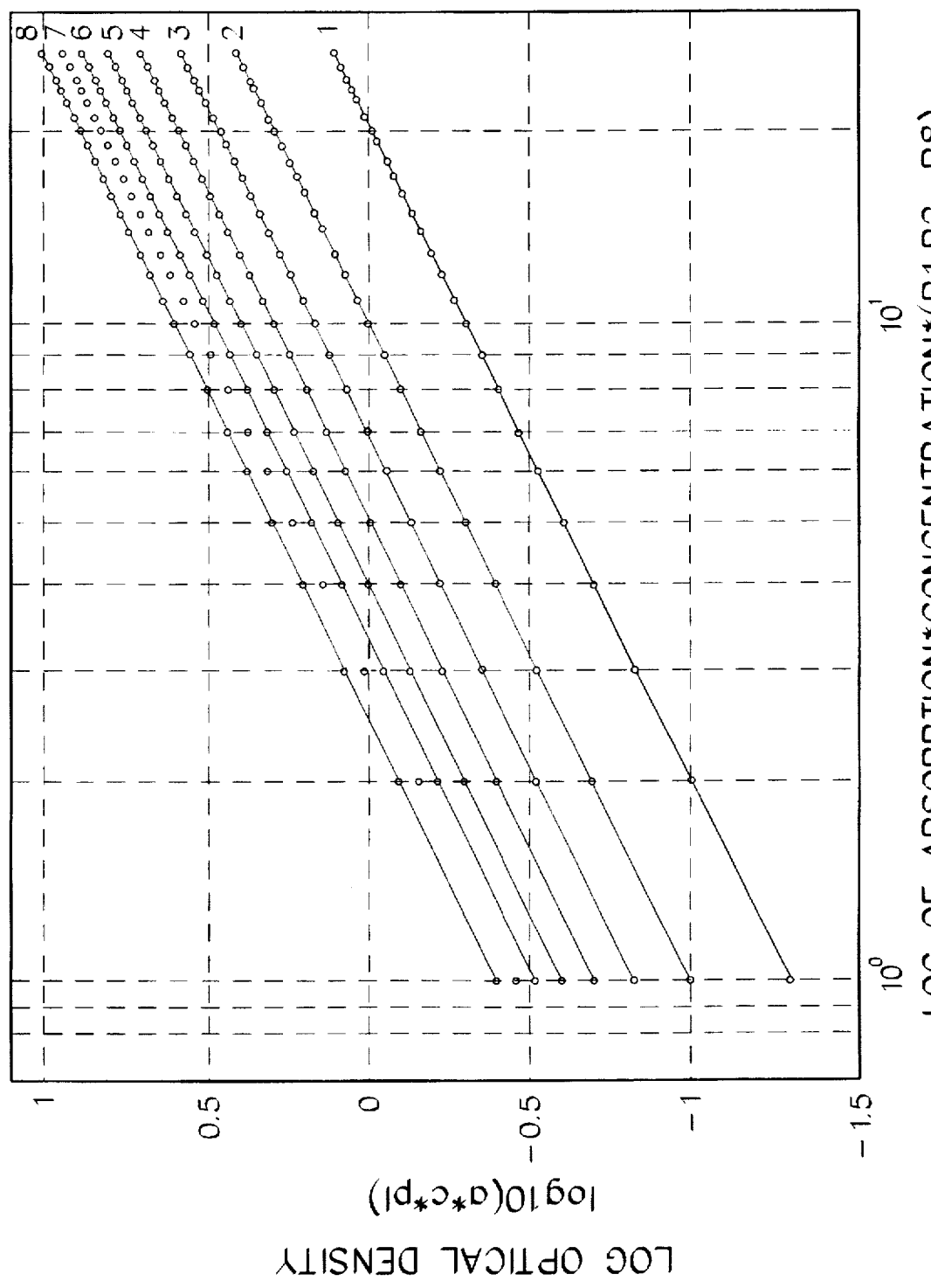
FIG. 6C illustrates a plot of the second log of the transmicivity through an optical medium versus the logarithm of the product of the absorption coefficient of the medium, the concentration of the medium, and the path length through the medium.
Figure 8:
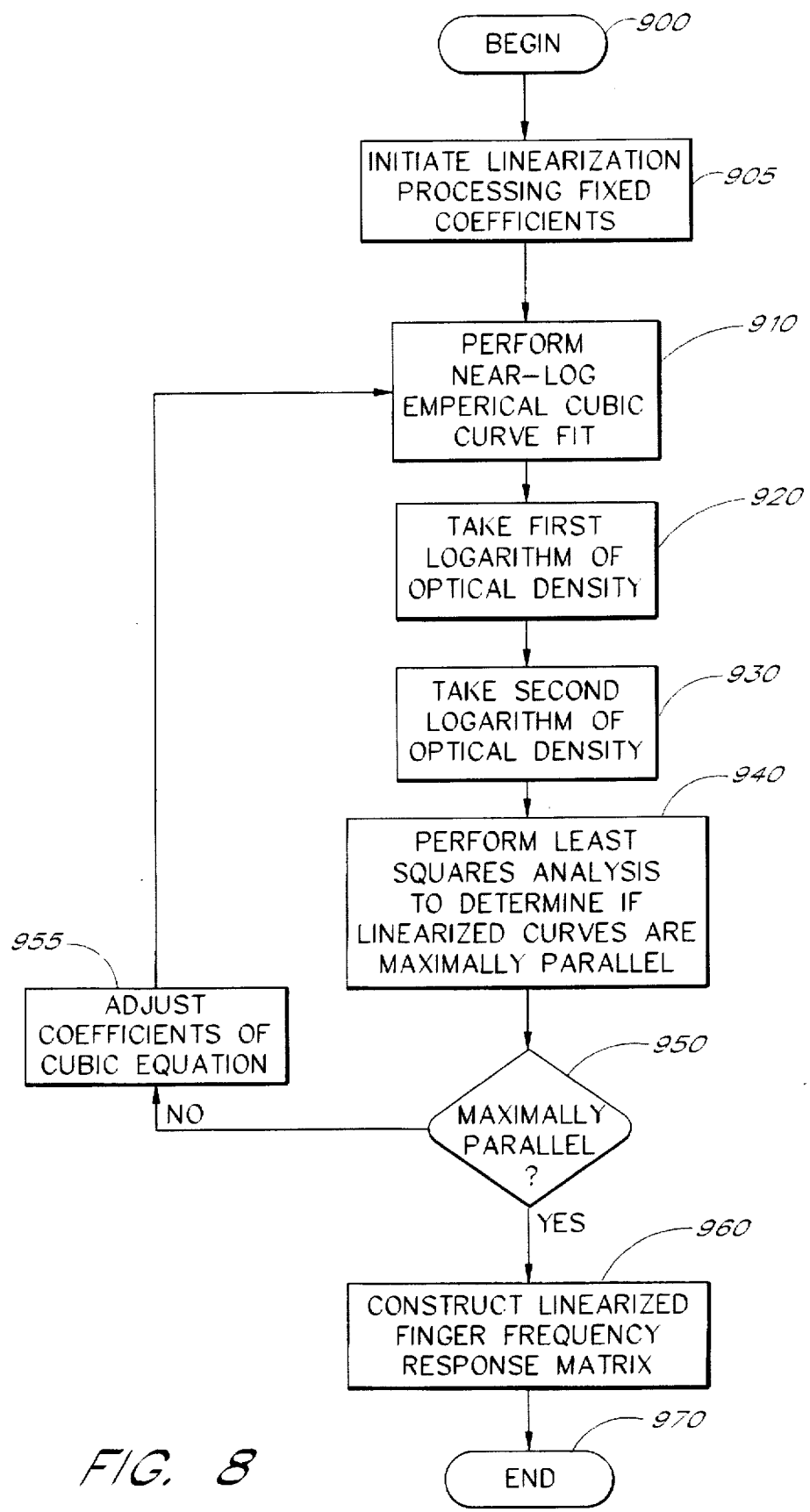
FIG. 8 is a flowchart which depicts in greater detail the method user in accordance with the present invention to linearize values within the finger optical response matrix as indicated within a subroutine block of FIG. 3.

FIGS. 6A–6C together with FIG. 8 depict the method used in accordance with the present invention to linearize the values within the transmission vector, $T(\lambda)$. As depicted in FIG. 6A, the percentage transmission of optical radiation at a particular wavelength (each curve representing a different path length P1, P2, etc.) is plotted versus the product of the absorption coefficient and the concentration of the optical medium through which the optical radiation passes. Thus, the curve of FIG. 6A indicates the relation between how much light is transmitted through a given pathlength of a medium, and the concentration of a given substance within the medium. A total of eight curves are shown in the graph of FIG. 6A wherein each curve indicates a different path length (e.g., P1, P2, ... P8) of light through the medium.

As is well known in the art, some optical radiation which passes through an optical medium such as the finger 130 passes immediately through the medium without substantial scattering so that the path length observed by that portion of optical radiation is approximately the same as the thickness of the finger. In other cases however, the optical radiation scatters within the medium so that the effective path length observed by these portions of the optical radiation is substantially longer than the thickness of the optical medium. It has been found that the average path length observed through an optical medium such as the finger 130 is typically three to five times the thickness of the finger 130. It is important that a linear relation exist among the several path lengths of optical radiation through an optical medium such as the finger 130 in order to insure that any given path length results in the same relation between the concentration of a substance within the medium and the optical characteristics of the medium. If a linear relation does not exist for various path lengths, a set of linear equations is not obtainable and the solution derived from the matrix equations will not be accurate.

As shown in FIG. 6A, a linear relation does not exist among the several path lengths of optical radiation through an optical medium. Rather, each of the eight curves depicted in FIG. 6A indicate a logarithmic relationship between the transmission percentage through the optical medium, and the product of the absorption coefficient and the concentration of the substance within the medium. As a result of this non-linearity, no representative average spectrum (i.e., one which is substantially path length independent) can be obtained. For example, a signal through a path twice as long will typically be attenuated by a factor of 1000 times, so that in an average its sum would be inconsequential.

If the characteristics of the medium were such that Beer-Lambert's law held precisely (i.e., the curves depicted in FIG. 6A were perfect exponentials), then a simple logarithm could be used to reduce the transmission vector $T(\lambda)$ to a set of linear equations. However, due to Rayleigh scattering and multiple constituents within the finger 130, the intensity of the optical radiation which passes through the finger are not related according to a strict application of Beer-Lambert's law. This is shown in FIG. 6A by a curve 601 which represents an actual, non-exponential relation between the transmission percentage and the product of absorption, concentration and path length. The difference between the curve 601 and the idealized exponential curve 1 is represented by the shaded area in FIG. 6A.

In order to transform the relation between transmission percentage and the product of absorption, concentration and path length depicted in FIG. 6A to a more linear relation, a cubic curve fit is performed on the actual transmission vectors to bring them into conformance with the exponential curves depicted in FIG. 6A, which is near to taking the logarithm of the transmission percentage. That is, a cubic fit equation is used to bring the curve 601, for example, in conformance with the exponential curve 1. Thus, this cubic fit is described hereinafter as a "near-log." Over selected regions, a cubic equation may be defined so as to resemble, or closely approximate, a logarithmic curve. Since the actual relation among the values in the transmission vector $T(\lambda)$ is typically near logarithmic, this near-log (i.e., cubic) equation may be used in place of a logarithm to more accurately linearize the values within the transmission vector $T(\lambda)$. Of course, it will be understood that a fourth or higher degree equation may be used to provide more accurate linearization of the values within the transmission vector $T(\lambda)$. In one advantageous embodiment of the present invention, the near-log equation has been experimentally determined to be for transmission through an adult human finger.

$$OD = -2.8088*T^3 + 4.7801*T^2 - 3.4215*T + 1.1289$$

and is typically applied over the range from $T=0$ to $T=1$. The precise values for the coefficients in the near-log equation above may vary from application to application, and, advantageously, an empirical evaluation with a number of test samples is used to precisely define an equation for a given application.

Once a near-log has been taken of the transmission percentage as discussed above, the relationship between the near-log of the transmission and the absorption coefficient times the concentration of the substance within the optical medium is substantially exponential. Thus, by taking a logarithm of the resultant vector values, a linear relationship is observed between the values on each curve as depicted in FIG. 6B. Although the relationship shown in FIG. 6B between the near-log of the transmission and the absorption coefficient times the concentration is a linear one, the slopes of the lines corresponding to different path lengths is more or less steep depending on the path length (P1, P2, ... P8). Thus, a different relationship exists between the near-log of the transmission and the product of the absorption coefficient and the concentration based upon the path length through the medium. Thus, the path lengths will not result in a substantially identical output. That is, a set of path-length-invariant, linear equations has not yet been formed. In order to prevent any error due to accidental differences in path length (i.e., nonlinearity of the values within the transformed $T(\lambda)$ matrix), a second log (referred to hereinafter after as the second log) is taken of both the corrected transmission percentage and the product of the absorption coefficient and the concentration. It should be understood here that a near-log fit may also be used in place of the log, as required by the specific application to obtain the most linear values.

The effect of taking the second log is depicted in FIG. 6C. As depicted in FIG. 6C, each of the lines representing differing path lengths is parallel so that each of these lines bears substantially the same relationship to the log of the product of the absorption coefficient and the concentration as to the double log of the transmission percentage. That is, the values within the resultant linearized optical frequency response matrix $D(\lambda)$ are all linearly related so that a set of linear equations may be derived from each of the curves depicted in FIG. 6C. Finally, all information relating to the pathlength is removed by rotating the curves of FIG. 6C so that the curves are parallel to the x-axis (not shown).

The method of linearizing the optical frequency response matrix is outlined briefly in the flowchart of FIG. 8. As depicted in FIG. 8, control passes from a begin block 900 to an activity block 905, wherein the linearization process initiates using fixed coefficients that are experimentally determined before run-time. Once enough data is gathered on the patient, to determine that a minimum transmission variance is obtained (due to the pressing motion of the finger 130), control of the method passes to an activity block 910 wherein the near-log cubic curve fit is performed on the optical frequency response matrix. That is, each of the values within the transmission vector $T(\lambda)$ is substituted for "T" in the cubic equation:

$$OD = -2.8088 * T^3 + 4.7801 * T^2 - 3.4215 * T + 1.1289$$

to form a new, exponential matrix.

Once a near-log is taken of the optical frequency response matrix, the first logarithm is taken of the transformed vector values as indicated in an activity block 920. The result of the first logarithm is a matrix having values related to one another as depicted in FIG. 6B.

The second logarithm is taken of the optical frequency response matrix, resulting in the relation depicted in FIG. 6C, as represented in an activity block 930. That is, a logarithm is taken of each of the values within the matrix defining the values of FIG. 6B to obtain a set of linearly related-values.

A least-squares analysis is performed on the linearized values to determine if the lines defined by the matrix (see FIG. 6C) are maximally parallel as represented in an activity block 940. That is, the slopes of the lines are calculated and the sum of the squares of the differences between the calculated slopes serves as a measure of how parallel the lines are. An iterative process which involves varying the coefficients of the curve fit equation is used to determine if the lines are maximally parallel, or at least parallel enough to obtain a viable glucose measurement.

Thus, as represented by a decision block 950, a test is performed to determine if the lines are parallel. If the lines are not parallel, then control passes to an activity block 955 wherein the values of the coefficients of the cubic fit equation are adjusted. In one embodiment, the value of one coefficient, beginning, for example, with the added constant, is increased or decreased by a fixed increment during successive iterations of the adjustment routine (i.e., each time the block 955 is entered from the block 950). Control then returns to the activity block 910 to apply the modified cubic fit equation to the vector values. The process repeats and a new indication is obtained of the parallelness of the lines. If the lines have become more parallel, then a further adjustment of the same coefficient is made in the same direction by the same or smaller increment. This continues until the lines no longer become more parallel. If it is determined that the lines become less parallel based upon an adjustment, then the same coefficient is adjusted in the opposite direction (i.e., if the adjusted coefficient was first increased, it is subsequently decreased). This is repeated until a relatively small change is observed in the parallelness of the lines upon successive adjustments of that coefficient. Adjustments are then made to the next coefficient (e.g., the coefficient on the first order term) in the same manner. Once this process has been repeated for each coefficient, the decision block 950 determines if the parallelness of the lines defined by the linearized vector is sufficient to produce a viable blood glucose measurement.

In a preferred embodiment, an indication is also given of the certitude of the glucose determination based upon the measured parallelness of the lines of FIG. 6C. This measure of certitude may, for example, be displayed together with the glucose measurement on the display screen 1320 (see FIG. 12). If it is determined within the decision block 950 that the measurement is not viable, an error signal may be generated, for example, by means of a warning light and a new set of measurements is taken to replace the non-viable values within the vector.

Once the optical density vector has been linearized, the linearized optical frequency response matrix, $D(\lambda)$, is constructed, as indicated in an activity block 960. Control then passes to an end block 970.

OVERALL SIGNAL FLOW

Figure 9:
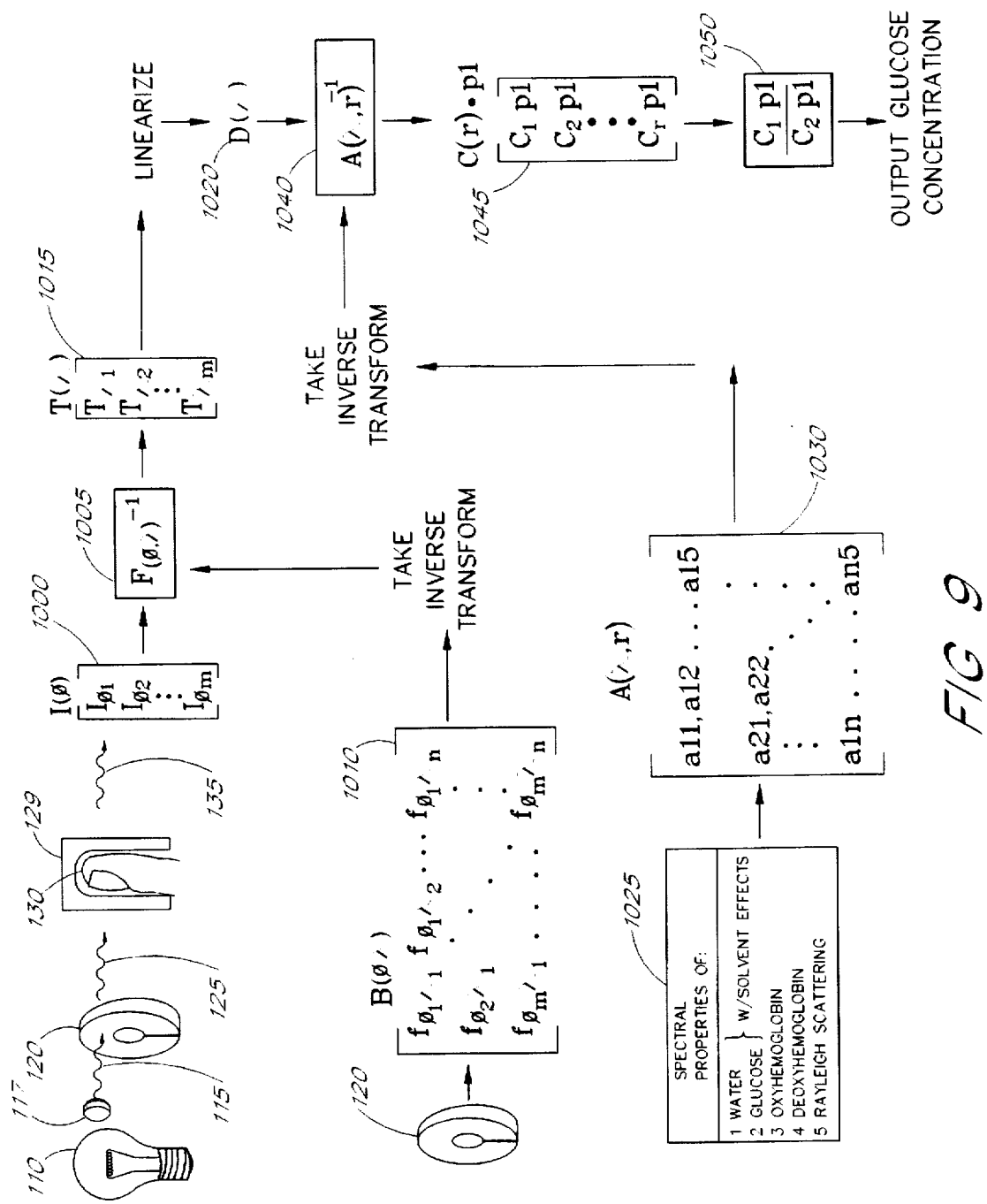
FIG. 9 is a data flow diagram which schematically represents the processing steps performed on an optical signal in order to determine glucose concentration based upon the illumination Of a fleshy medium by the optical signal.

FIG. 9 is a schematic diagram which pictorially represents the overall data flow used in accordance with the teachings of the present invention to obtain blood glucose concentration by means of optical signal processing. As shown in FIG. 9, the light source 110 emits light 115 which passes through the lens 117 and the filter 120 to provide filtered optical radiation 125. The optical radiation 125 passes through the finger 130 to provide an optical signal 135 used to generate a signal intensity matrix 1000.

The signal intensity matrix 1000 is multiplied by the inverse of a filter characteristic matrix 1010 as indicated within a block 1005. As shown in FIG. 9, the filter characteristic matrix 1010 is derived from an analysis of the filter 120, as described above with reference to FIGS. 4A–4D and FIG. 7. The inverse transform of the filter characteristic matrix 1010 is multiplied by the signal intensity vector 1000 to obtain the optical frequency response matrix, or transmission vector, 1015. The optical frequency response matrix 1015 is then linearized as described above with reference to FIG. 6A–6B and FIG. 8, to obtain the linearized signal strength matrix, or linearized optical density vector, 1020.

The several spectral properties of water, glucose, oxyhemoglobin, deoxyhemoglobin, and scattering as represented within the table 1025, are used to construct a blood constituent matrix 1030. The inverse transform is taken of the blood constituent matrix 1030 to obtain an inverse blood constituent matrix as indicated within the block 1040. The inverse blood constituent matrix is multiplied with the signal strength matrix 1020 to obtain a blood concentration times path length vector 1045.

A ratio is taken between the element of the vector 1045 indicating glucose concentration times path length and the element in the vector 1045 indicating water concentration times path length as indicated within a block 1050. This ratio results in the concentration of glucose in water, which is equivalent to blood glucose, and is output as a data value representing glucose concentration.

METHOD OF PRODUCING THE OPTICAL FILTER

FIG. 10 depicts schematically the general method used in accordance with the present invention to manufacture the optical filter 120. It should be first noted that previous methods employed to fabricate such optical filters typically involved laying out a circular substrate and then selectively increasing the coating thicknesses on the surface of the circular substrate as the substrate is rotated with uniform speed.

Figure 13:
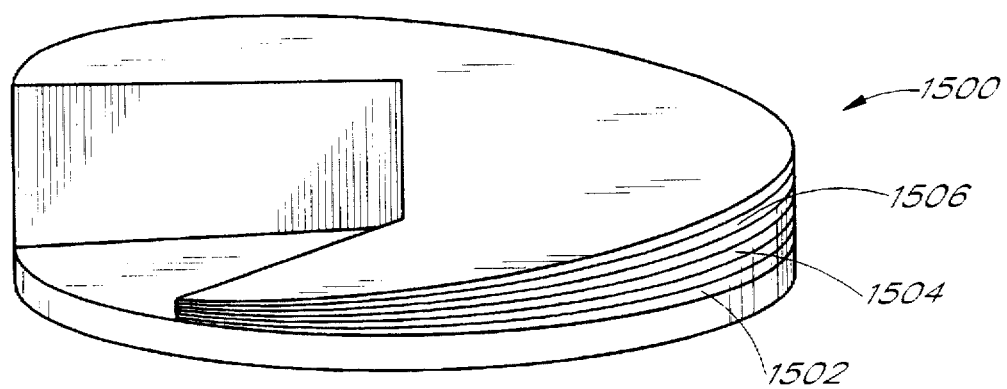
FIG. 13 depicts a dichroic filter as constructed by conventional methods.

Such a filter 1500 is depicted in FIG. 13 as having coating layers 1502, 1504, 1506, etc., of increasing thicknesses to form a spiral configuration as the filter 1500 is rotated. Of course, it should be understood that the coating thicknesses depicted in FIG. 1 are exaggerated for ease of illustration. This method of optical coating is carried around substantially the entire circumference of the circular substrate so that as the coated substrate revolves, the thickness of the optical coating grows throughout the entire revolution and then suddenly drops back from the thickest coating to the thinnest coating at the end of one revolution.

It has been found, however, that such methods of optical coating require high precision and are extremely costly. Furthermore, manufacturing these filters is typically carried out one-by-one, since production methods do not allow for laying out several disks on a single sheet for mass production purposes.

In accordance with the manufacturing method of the present invention, a flat substrate 1100 is coated with optical coating of increasing thickness to form wedge-shaped coated layers 1110. Of course, it should be noted that for purposes of clearly illustrating the present invention, the thickness of the optical coating 1110 has been exaggerated, and in practical applications the thickness of the optical layer 1110 will vary from 1.66 micrometers to about 3.33 micrometers, with an average thickness of about 2.35 micrometers. Of course, it will be understood that these thicknesses are approximate and may vary depending upon the index of refraction of the layer materials.

Such a method allows for deposition of a minimal number of optical coating layers. In one preferred embodiment, only 17 layers are necessary to obtain the desired resolution. In one embodiment, alternating layers of high (2.20) and low (1.48) indices of refraction are deposited onto the substrate. Although the manufacturing method of the present invention may result in less perfect filters than other more expensive procedures, such imperfections can be accommodated in digital signal processing steps as described above. For example, previous filters typically pass a single frequency band at a time, while the filter of the preferred embodiment may allow for multiple bands to pass, since this is accounted for by the signal processing of the invention.

Once the optical layer 1110 has been applied to the substrate 1110, a cylindrical portion 1120 is cut from the wedge-shaped slab formed by the optical layer 1110 together with the substrate 1110. A cylindrical aperture is then formed inn the center of the cylindrical portion 1120 to form the filter 120 and, subsequently, an optically opaque strip such as the brass strip 122 is formed over a portion of the optical filter disk 120.

The above description provides ease of illustration for understanding the essential aspects of the invention. However, it should be understood that the method may, in practice, involve first cutting the substrate into a disk with a shaft. Thereafter, the optical coatings are applied onto the disk as though the disk were still square so that the excess falls onto the platform (not shown) supporting the disk within the vacuum tank. In this manner the wedge is formed on the surface of the disk 120 as shown in FIG. 10.

In one advantageous embodiment, the production specifications for the filter 120 are as follows:

SIZE: 20 mm wide×20 mm wavelength span, linear multilayer coating
SUBSTRATE: 25 mm OD glass disc with 7.5 mm shaft hole in center
WAVELENGTH: 700–1400 nanometers
1/2 BW: 50 to 200 nanometers, bands may repeat
BLOCKING: none
ENVIRONMENT: Survive condensing humidity, 0–70 c The pass band edges are produced so as to differentiate a 20 nanometer band edge.

The pass band may repeat within the window at as little as 400 $cm^{-1}$ spacing, or 17–18 periods within the window. The pass band center transmission should approach 100%, and the region between pass bands should approach 100% reflection.

Blocking requirements outside of the window are not critical. They may be limited by absorption or band-edge materials such as RG660, RG700, or semiconductors, or O-H bands typically found in glass below 7100 $cm^{-1}$.

Only the ability to resolve wavenumber bands near 200 $cm^{-1}$ with one or more band edges should limit the cost. The system is cost sensitive to the filter disc for production quantities of 1,000 to 100,000 per year.

Characteristics for Present Embodiment

Preferably, the filter will not have a window narrower than 8,000 to 11,000 $cm^{-1}$ or about 910 to 1,250 nm. The bandwidth is advantageously wider than 200 $cm^{-1}$, and the band edge is advantageously narrower than 200 $cm^{-1}$. The transmission maximum of the primary band is advantageously above 80%, and the transmission minimum is advantageously below 20%. Any other bands should be repeatable, unit to unit; but if they are not, a calibration ROM could be used in accordance with the DSP to perform initial calibration of individual filters.

Mechanical Boundaries and Characteristics

The linear filter is advantageously rotated about its center at less than 4,800 RPM, with an aperture centered at a radius of minimum 9 mm to maximum 45 mm, with a clear aperture diameter of 1 mm to 3 mm and a numerical aperture of 0.12 to 0.40. The light path passes through an annular region of the rotating filter, causing a sinusoidal scan of the wavelengths, although they are deposited linearly.

For dynamic balance and low turbulence, the linear filter is deposited on a circular substrate. Since the center is not used optically, a standard diameter shaft mounting hole is preferred; most of the present hardware in the invention use either 0.5000–0.000, +0.0005" diameter, or 7.5–0.0+0.1 mm. For a small filter, e.g., 20 mm diameter, bonding to the uncoated side would be considered. Note that the filter mount does not have spokes or other structural interruption of the optical path.

Initial optical-mechanical alignment of the coating on the glass is not critical beyond 0.5 mm and will be established electronically. Some marking of the deposit alignment at the edge or center is desired.

Overall Sequence of Data Processing

The following is a summary of the sequence of steps used to process the data signals detected by the detector 140. As described above, the sequence of signal processing is extremely important for obtaining an accurate measurement of the patient's blood glucose level. Significant signal processing and analysis is wasted in previous systems which did not employ the proper sequence.

The Instructment System

The signal generation begins with light source and finger transmission properties. For the glucose sensor, start with the received transmission, and perform inverse operations on the signal until only the desired parameter is left. Note that the inverse operations are only numerically equivalent, not the inverse functions of mathematically analytical functions. Each operation is some transformation which re-organizes the data without convolving or otherwise mixing the signal with the noise. The information content of the signal should not be decreased or corrupted at any stage. Many spectroscopic instruments fail this criterion. Thus, this system design is intended to be unique in this field by being in the appropriate order, with a clear objective that avoids corrupting signal operations.

1. Test Transducer Signals

Perform Signal and Noise Classification: Synchronous signals correlated in model bounds are deterministic (with the same autocorrelation features) and stochastic (random added noise with no autocorrelation features beyond Gaussian).

Specifically, each new received spectrum is added to the data matrix block until the classifier detects a new noise distribution, or any significant change (detected by means of a statistical test) in the correlation matrix of the 15 non-zero wavelengths. When a change occurs, it indicates that the finger 130 has changed to a new position, or that a new finger has been inserted, or that a new patient is in the optical path. If block-matrix algebra is being used, then at this change, the system stops adding to the old block and starts creating a new block, at least 15 samples long, to perform statistical tests on data set.

If a recursive method is used, the recursion time constant (sample number) is shortened when the classifier detects a sample change until noise increases to a set statistical limit, or the block receives the minimum number of samples (typically equal to the number of wavelengths resolved, 15 or 16).

Each answer displayed by the glucose sensor and computer will be the result of one block (of variable length), or of a length set by any recursion process's time constant. Whenever the patient changes finger position, fingers, or even patients, the system observes the change, and starts a new calculation of parameters, including glucose concentration. Thus the patient and doctor can have confidence in the readout by knowing every time the properties change, the instrument generates fresh data. At the same time, this feedback to the patients encourages the patient to remain steady during the necessary analysis time. For the present signal-to-noise ratios, and for the amount of time a patient is expected to remain steady, the analysis time should be on the order of 3 to 30 seconds. When used as a continuous monitor, longer stable periods will be available, and averages on the order of 30 to 180 seconds might be typical.

2. Clean-Up Electronic Noise

Perform the first linear operations to remove electronic noises: subtract linear interference and average random noise.

Deterministic noise may be adapted to, and subtracted due to a persistent, periodic form and phase; stochastic noise, such as impulses, start-up transients, or white noise spectra, have no predictable properties. Model signals of a priori information become first approximations, and are loaded into any adaptive or recursive filters at start-up, and are used to predict signals through any impulsive or transient noise. This is the general form of a low-pass filter, but with the feature of averaging the shape of entire waveforms in a heartbeat vector (e.g., a heartbeat plethysmographic (equal to pressure, volume) waveform as a vector with one average beat-to-beat period of systolic, dicrotic, and diastolic shapes). The noise in this waveform is preferably averaged to zero.

At the detector 140, ambient light, powerline noise at 60, 120, etc. Hz, electrostatic, and magnetic fields, and electromagnetic waves are added to the signal photons coming through the patient finger. These noises are filtered, subtracted or averaged-to-zero before any non-linear stage is encountered.

When all linear relationships are removed, only nonlinear relationships remain. The next operation is a nonlinear transform. Subsequently, linear operations are performed again. The last step is a linear output of some parameter, so the preceding steps are a sequence of linearizations followed by linear operations to uncover signals in interference and noise.

The industry standards use light-source carrier-modulation to get away from 60, 120 Hz (50, 100 outside USA), and narrow band filtering around the carrier. Such a frequency filter does not remove out of phase noise. Direct subtraction of a best fit noise model with matched phase removes all ambient interference.

3. Prepare Linear Solution

Linearization, Log Transforms: The object of the operations is to orthogonalize (make statistically independent; make normal; decorrelate) the desired signal from a succession of added, multiplied, or distorting noises, until only the desired signal remains.

If the signal is not linear, then it may have multiple values for the inverse. Then, no operator or process can discriminate the answers.

4. Linear Algebra

Perform matrix algebra on Linear data: Standard spectroscopic matrix algebra solutions are used after all of the assumptions for linear relationships and for stationary signal and noise distributions are satisfied.

5. Test Physiological Signals

Perform error detection: determine amplitude, frequency boundaries, and correlate these with any a priori interferences to continue signal and noise classification.

6. Feedback

Feedback to classification, linearization or physiological noises: Subtract any linear interference and average the random noise.

7. Feedforward

Apply clinical algorithms and generate derived parameters.

8. Test Clinical Limits, Alarms

Define the finger 130 in the optical path. Test if it is mostly water with large scattering extinction, (about 30db loss/10 mm is typically observed), check the pulse, correlate with previous records to identify the patient and the characteristics of the patient's finger. Display "Not a healthy finger" or equivalent, but do not stop operating since calibration tests may be done with in vitro materials. If any unusual correlations or signals are present, display increasing number of auxiliary parameters as a test, and for user credibility.

9. I/O, Commands, Clinical Data, Display, Record

This portion relates to input keys, input data and output format. Glucose tolerances as well as other parameters and historical records are input. Other embodiments may also require input of diagnosis, predictions, instructions per prescription, etc. All of the clinical data required to manage a diabetic diet, such as the lessons from the Diabetic Complications and Control Tests (DCCT), can be eventually put into the program. This data may be programmed into a personal computer to minimize the sensor computer.

Although the preferred embodiment of the present invention has been described and illustrated above, those skilled in the art will appreciate that various changes and modifications to the present invention do not depart from the spirit of the invention. For example, the principles and method of the present invention could be used to detect trace molecules within the bloodstream (e.g., for drug testing, etc.). In addition, a single near-log equation of sufficient accuracy may be used to linearize the optical frequency response matrix. Accordingly, the scope of the present invention is limited only by the scope of the following appended claims.

What is claimed is:

1. A system for noninvasively monitoring blood glucose concentration within the bloodstream of a subject, said system comprising:

a light source which emits light radiation at a plurality of wavelengths;

a receptacle for receiving a fleshy medium carrying blood of said subject;

an optical detector positioned to receive light radiation from said light source which has passed through and been attenuated by said fleshy medium and said blood, said optical detector responsive to the attenuated light radiation to generate an output signal indicative of the intensity of said light radiation after attenuation by said fleshy medium and said blood; and a signal processor coupled to said detector to receive said output signal, said signal processor responsive to said output signal to isolate portions of said output signal due to optical characteristics of said fleshy medium from portions of said output signal reflecting the optical characteristics of said blood, said signal processor providing a set of frequency response values reflecting the optical characteristics of said blood;

a linearization module executable by said signal processor to linearize said set of frequency response values; and a glucose concentration determination module executable by said signal processor to determine the concentration of glucose within said patient's bloodstream based upon the linearized frequency response values.

2. The system of claim 1, wherein said light source comprises a plurality of emitters, each emitter transmitting light at a selected one of said plurality of wavelengths.

3. The system of claim 1, wherein said light source comprises a broadband light source, said system further comprising an optical filter which selectively passes subsets of said plurality of wavelengths.

4. The system of claim 3, wherein said detector comprises a single detector responsive to said subsets of said plurality of wavelengths to provide an output signal indicative of the sum of the intensities of said subsets of said plurality of wavelengths after attenuation by said fleshy medium and said blood.

5. The system of claim 1, wherein said optical detector comprises a plurality of detectors, each detector responsive to at least one of said plurality of wavelengths to generate an output signal indicative of the intensity of said at least one wavelength.

6. The system of claim 1, wherein the linearization module comprises a double logarithm operation.

7. A system for noninvasively monitoring blood glucose concentration within a patient's bloodstream via spectroscopic measurement of attenuation of a fleshy medium containing blood, said system comprising:

a light source which emits optical radiation at a plurality of wavelengths;

a variable optical filter which in a first position selectively passes a first subset of said plurality of wavelengths, said filter movable from a first position to a second position to pass a second subset of said plurality of wavelengths;

an optical detector positioned to receive light from said light source which has been filtered by said filter and attenuated by said fleshy medium and said blood, said optical detector responsive to light wavelengths of at least said first and second subsets to generate an output signal indicative of the sum of intensities of the optical radiation filmed by said filter and attenuated by said fleshy medium and blood; and a signal processor coupled to said detector to receive said output signal;

an isolation module executable by said signal processor to isolate portions of said output signal due to optical characteristics of said optical filter and due to said fleshy medium from portions of said output signal reflecting the optical characteristic of said blood to analyze said portions reflecting the optical characteristics of said blood to determine the concentration of glucose within said patient's bloodstream.

8. A method of noninvasively determining blood glucose concentration comprising the steps of:

generating a set of values indicative of optical characteristics of significant blood constituents, one of said values indicative of the optical characteristics of glucose dissolved in water;

illuminating a fleshy medium having blood with light of a plurality of wavelengths;

detecting said light after attenuation of said light by said fleshy medium and said blood;

generating a signal from said detected light, said signal indicative of optical characteristics of said fleshy medium and said blood;

isolating components of said signal which are indicative of the concentration of glucose dissolved in water within said blood in response to said detected light and said set of values indicative of optical characteristics of said significant blood constituents; and generating a value indicative of the glucose concentration within said blood.

9. The method of claim 8, wherein said significant blood constituents comprise water, hemoglobin, oxyhemoglobin and glucose dissolved in fluid.

10. A method of noninvasively determining a concentration of a blood constituent comprising the steps of:

illuminating a living medium having blood with optical radiation, wherein the blood has a concentration of the blood constituent and the optical radiation traverses at least one path length through the medium;

detecting the optical radiation to produce electrical signals indicative of optical characteristics of the medium and the blood;

in response to said electrical signals, generating a first set of values indicative of the optical characteristics of the medium and the blood;

taking a logarithm of the first set of values to generate a second set of values;

taking a logarithm of the second set of values to obtain a linearized set of values that are indicative of the concentration of the blood constituent; and calculating the concentration of the blood constituent based upon the linearized electrical signals.

11. The method of claim 10, wherein said indication of the concentration does not vary significantly with respect to the path length through the medium.

12. A method as defined in claim 10, wherein the blood constituent comprises blood glucose.

13. The method of claim 10, wherein said concentration of the blood constituent does not vary significantly with respect to the path length through the medium.

14. A method as defined in claim 10, wherein said linearizing step further comprises the step of transforming the first set of values using a polynomial equation to provide a transformed first set of values.

15. A method of analyzing a concentration of a blood constituent from an optical signal incident upon a fleshy medium having blood, the method comprising the steps of:
   filtering the optical signal with a filter having known spectral characteristics;
   detecting the optical signal after attenuation from said fleshy medium to generate a signal having a set of values indicative of optical characteristics of the fleshy medium and said blood;
   removing components of the signal quantity due to electrical noise;
   removing components of the signal due to nonblood constituents of the fleshy medium;
   linearizing the signal to generate a set of linearly related values indicative of the concentration of the blood constituent;
   deconvolving components of the electrical signal due to the filter prior to the step of solving for the blood constituent concentration; and
   solving the linearly related values for the blood constituent concentration.

16. A method as defined in claim 15, wherein said deconvolving step further comprises the steps of:
   generating a set of values indicative of the transmitted signal intensity to obtain a signal intensity matrix;
   generating a set of values indicative of the spectral characteristics of the filter to obtain a filter characteristics matrix;
   taking an inverse transform of the filter characteristics matrix; and
   multiplying the inverse transform of the filter characteristics matrix with the signal intensity matrix to obtain a matrix indicative of the optical characteristics of the fleshy medium and blood.

17. A method of analyzing a concentration of a blood constituent from an optical signal incident upon a fleshy medium having blood, the method comprising the steps of:
   detecting the optical signal after attenuation from said fleshy medium to generate a signal having a set of values indicative of optical characteristics of the fleshy medium and said blood;
   removing components of the signal quantity due to electrical noise;
   removing components of the signal due to nonblood constituents of the fleshy medium;
   linearizing the signal to generate a set of linearly related values indicative of the concentration of the blood constituent;
   generating a spectral library containing values indicative of spectral characteristics of components of the blood including the blood constituent;
   generating a set of linear equations having coefficients based upon said values indicative of the spectral characteristics of components of the blood; and
   solving the linear equations to obtain a value indicative of the concentration of the blood constituent.

18. A method as defined in claim 17, wherein the blood constituent comprises glucose.

19. A method as defined in claim 17, wherein the step of generating the spectral library includes the step of observing the spectral characteristics of a known concentration of glucose dissolved in water or blood to determine the spectral characteristics of glucose dissolved in water.

20. A method of noninvasively determining a concentration of a blood constituent comprising the steps of:
   illuminating a living medium having blood with optical radiation, wherein the blood has a concentration of the blood constituent and the optical radiation traverses at least one path length through the medium;
   detecting the optical radiation to produce electrical signals indicative of optical characteristics of the medium and the blood;
   in response to said electrical signals, generating a first set of values indicative of the optical characteristics of the medium and the blood;
   taking a logarithm of the first set of values to generate a second set of values;
   taking a logarithm of the second set of values to obtain a linearized set of values that are indicative of the concentration of the blood constituent; and
   calculating the concentration of the blood constituent based upon the linearized set of values.

21. A method of noninvasively determining a concentration of a blood constituent comprising the steps of:
   illuminating a living medium having blood with optical radiation, wherein the blood has a concentration of the blood constituent and the optical radiation traverses at least one path length through the medium;
   filtering the optical signals with a filter having known spectral characteristics;
   detecting the optical radiation after attenuation through said living medium and said blood to produce electrical signals indicative of the optical characteristics of the medium and the blood;
   linearizing the electrical signals;
   deconvolving components of the electrical signal due to the filter; and
   calculating the concentration of the blood constituent based upon the linearized and deconvolved electrical signals.

22. The method as defined in claim 21, wherein said deconvolving step further comprises the steps of:
   generating a set of values indicative of the spectral characteristics of the filter to obtain a filter characteristics matrix;
   taking an inverse transform of the filter characteristics matrix; and
   multiplying the inverse transform of the filter characteristics matrix with a matrix indicative of the optical characteristics of the fleshy medium and the blood.

* * * * *

UNITED STATES PATENT AND TRADEMARK OFFICE
CERTIFICATE OF CORRECTION

PATENT NO. : 5,743,262
DATED : April 28, 1998
INVENTOR(S) : James Lepper, Jr. and Mohamed K. Diab It is certified that error appears in the above-identified patent and that said Letters Patent is hereby corrected as shown below:

In claim 7, column 32, line 7, "filmed by" should be changed to "filtered by"

Signed and Sealed this

Fifth Day of January, 1999

Attest:

Attesting Officer

*Acting Commissioner of Patents and Trademarks*